(12) United States Patent
Srivastava et al.

(10) Patent No.: US 9,969,764 B2
(45) Date of Patent: May 15, 2018

(54) DITHIOLANE FUNCTIONALIZED NUCLEOSIDE AMIDITES AND SUPPORTS FOR STRONGER IMMOBILIZATION OF BIO-MOLECULES ON SOLID SURFACES

(71) Applicant: ChemGenes Corporation, Wilmington, MA (US)

(72) Inventors: Suresh C Srivastava, Burlington, MA (US); Santhosh K Thatikonda, Woburn, MA (US); Sant K Srivastav, Burlington, MA (US); Praveen K. Shukla, Burlington, MA (US); Alok Srivastava, Burlington, MA (US)

( * ) Notice: Subject to any disclaimer, the term of this patent is extended or adjusted under 35 U.S.C. 154(b) by 0 days. days.

(21) Appl. No.: 15/132,417

(22) Filed: Apr. 19, 2016

(65) Prior Publication Data

US 2017/0037076 A1    Feb. 9, 2017

Related U.S. Application Data

(63) Continuation of application No. PCT/US2014/061850, filed on Oct. 22, 2014.

(60) Provisional application No. 61/894,872, filed on Oct. 23, 2013.

(51) Int. Cl.

| | | |
|---|---|---|
| C07H 19/00 | (2006.01) | |
| C07H 21/00 | (2006.01) | |
| C07H 19/16 | (2006.01) | |
| C07H 19/06 | (2006.01) | |
| C07H 19/067 | (2006.01) | |
| C07H 19/073 | (2006.01) | |
| C07H 19/167 | (2006.01) | |
| C07H 19/173 | (2006.01) | |

(52) U.S. Cl.
CPC ............. *C07H 19/16* (2013.01); *C07H 19/06* (2013.01); *C07H 19/067* (2013.01); *C07H 19/073* (2013.01); *C07H 19/167* (2013.01); *C07H 19/173* (2013.01)

(58) Field of Classification Search
None
See application file for complete search history.

(56) References Cited

U.S. PATENT DOCUMENTS 6,821,529 B2 * 11/2004 Nelson .................. A61K 31/50
424/450

OTHER PUBLICATIONS

Guillonneau et al. European Journal of Medicinal Chemistry (2003), vol. 38, pp. 1-11.*
"Representative." oxforddictionaries.com. Oxford Dictionary, n.d. Web. Mar. 23, 2017.*

* cited by examiner

*Primary Examiner* — Patrick T Lewis
(74) *Attorney, Agent, or Firm* — Harvest IP Law LLP

(57) ABSTRACT

This invention is related to nucleic acid chemistry and describes novel 1,2-dithiolane functionalized nucleoside phosphoramidites (1, Chart 1) and corresponding solid supports (2, Chart 1). In addition to these derivatives, 1,2-dithiolane moiety can also be functionalized to at the various positions of the nucleobase and sugar part as shown in Schemes 1 to 8. The nucleosides of our invention carry a primary hydroxyl for DMTr (4,4'-dimethoxytrityl) function for chain elongation. Furthermore, the phosphoramidite function is attached at the 3'-hydroxyl of the nucleoside. This allows oligonucleotide chain extension under standard DNA and RNA synthesis chemistry conditions and techniques, thus leading to high quality oligonucleotides. These derivatives are useful for introduction of reactive thiol groups either at 3'- or 5'-end of the oligonucleotides on the solid supports such as gold, silver and quantum dots.

14 Claims, 14 Drawing Sheets

Figure 2

| Peak No | Peak Name | Ret Time (min) | Peak Area (counts) | Result (Area %) |
|---|---|---|---|---|
| 1 | | 4.543 | 156723 | 0.16 |
| 2 | | 11.470 | 97053376 | 99.71 |
| 3 | | 13.573 | 130161 | 0.13 |
| | Totals | | 97340256 | 100.00 |

Figure 6

| Peak No | Peak Name | Ret Time (min) | Peak Area (counts) | Result (Area %) |
|---|---|---|---|---|
| 1 |  | 2.032 | 78514 | 0.11 |
| 2 |  | 3.018 | 40015 | 0.06 |
| 3 |  | 3.409 | 66481 | 0.10 |
| 4 |  | 3.911 | 148449 | 0.22 |
| 5 |  | 4.292 | 122827 | 0.18 |
| 6 |  | 4.592 | 23864 | 0.03 |
| 7 |  | 4.793 | 12510 | 0.02 |
| 8 |  | 4.989 | 132415 | 0.19 |
| 9 |  | 5.646 | 55362 | 0.08 |
| 10 |  | 6.527 | 67095084 | 97.32 |
| 11 |  | 9.521 | 127201 | 0.18 |
| 12 |  | 12.600 | 614111 | 0.89 |
| 13 |  | 15.189 | 428493 | 0.62 |
| Totals |  |  | 68945328 | 100.00 |

Figure 10

| Peak No | Peak Name | Ret Time (min) | Peak Area (counts) | Result (Area %) |
|---|---|---|---|---|
| 1 | | 10.092 | 160058 | 0.09 |
| 2 | | 10.184 | 54636 | 0.03 |
| 3 | | 10.326 | 342332 | 0.18 |
| 4 | | 13.667 | 533377 | 0.29 |
| 5 | | 14.924 | 87992984 | 47.22 |
| 6 | | 15.470 | 167345 | 0.09 |
| 7 | | 16.271 | 97113848 | 52.11 |
| Totals | | | 186364576 | 100.01 |

DITHIOLANE FUNCTIONALIZED NUCLEOSIDE AMIDITES AND SUPPORTS FOR STRONGER IMMOBILIZATION OF BIO-MOLECULES ON SOLID SURFACES

CROSS REFERENCE TO RELATED APPLICATIONS

This is a Continuation Application filed under 35 U.S. § 111(a), claiming benefit under 35 U.S.C. § 120 and § 365(c) of a Patent Cooperation Treaty Application PCT/US2014/061850, filed on Oct. 22, 2014, which in turn is based on, and claims the benefit of U.S. Provisional Patent Application No. 61/894,872, filed Oct. 23, 2013, which is incorporated herein by reference in its entirety.

FIELD OF THE INVENTION

This invention is related to nucleic acid chemistry and describes novel 1,2-dithiolane functionalized nucleoside phosphoramidites (1, Chart 1) and corresponding solid supports (2, Chart 1). These derivatives are useful for introduction of reactive thiol groups either at 3'- or 5'-end of the oligonucleotides on the solid supports such as gold, silver and quantum dots. Further advantage of these probes is that they have relatively long linker arm, which allows clean formation of the monomers on the solid surfaces and keeps the self-assembled monomers in the optimum distance from the solid support. The nucleosides of our invention carry a primary hydroxyl for DMTr (4,4'-dimethoxytrityl) function for chain elongation. Furthermore, the phosphoramidite function is attached at the 3'-hydroxyl of the nucleoside. This allows oligonucleotide chain extension under standard DNA and RNA synthesis chemistry conditions and techniques, thus leading to high quality oligonucleotides. Pairs of oligonucleotide-gold nanoparticle conjugates, due to dithiolane unit serve as unique probes for recognizing specific sequences in DNA segments, as building blocks for assembling novel structures, bio-diagnostics and nano technology based therapeutics.

BACKGROUND OF THE INVENTION

In recent years, development of nanometer-sized structures has received much attention for various molecular biological applications. Gold is probably the most suited element because it exhibits a high chemical stability (noble metal), is characterized by its ability to strongly absorb the visible light at definite wavelengths and is intrinsically not toxic. The thiol (R—SH) modified oligonucleotides serve as attractive tools with a vast number of potential applications in the field of nucleic acid chemistry such as it enables covalent attachment of variety of ligands that contain (a) α,β-unsaturated ketone; (b) maleimide; (c) other Michael acceptor groups; or (d) cysteines in proteins to make disulfide bonds. In addition to this, thiol has a strong specific interaction with gold surface to form reversible covalent bond with gold.

The reactive thiol group can be introduced into oligonucleotides by incorporating sulfide-modified phosphoramidite monomers during oligonucleotide synthesis. Generally, two different types of sulfide modified monomers viz disulfide strategy [Jones, D. S., Hachmann, J. P., Conrad, M. J., Coutts, S., Livingston, D. A. U.S. Pat. No. 5,391,785, 1995] or S-trityl protection [Connolly, B. A.; Rider, P. Nucleic Acids Res. 1985 13, 4485] are very popular to achieve this. Reactive thiol group from the disulfide is generated by treating oligonucleotides with reducing agent such as dithiothreitol (DTT). Whereas, in the other S-trityl strategy, it is generated by cleaving trityl group by silver nitrate. However, this strategy has clear disadvantage of elaborate cleavage process of trityl group with the silver nitrate, which results in relatively poor yields of the final oligonucleotide. Hence, disulfide modified phosphoramidites serve as superior probes for generating thiol groups. The most popular disulfide probes are with the general formula DMT-O—R—S—S—R—O—P(CE)(NiPr2), where R being C3 or C6 spacer arm [Jones, D. S., Hachmann, J. P., Conrad, M. J., Coutts, S., Livingston, D. A. U.S. Pat. No. 5,391,785, 1995]. Because of its interesting properties, we therefore carried out detailed investigation to develop a new synthetic and purification method which gives acyclic disulfide phosphoramidite (where R is C3 spacer) in a high purity for commercial, research and development. Our optimized synthetic protocol is reproducible, suitable for multi gram scale and yields target phosphoramidite in high purity by $^{31}$P NMR (>94%). [Srivastava, S. C.; Thatikonda, S. K.; Srivastav, S. K. Shukla, P. U.S. Patent Application No. 2012/000103, 2012].

Nuzzo and Allara have discovered that reactive thiol group adsorb on gold surface and forms ordered mono layers. [Nuzzo, R. G., Allara, D. L. Jour. Am. Chem. Soc. 1983, 105, 4481]. After this, oligonucleotides with thiol group are very much used to generate self-assembled monolayers (SAMs) on the gold surfaces. Although different molecules can be immobilized (silanes, carboxylic acids, pyridines, sulphites and thiols) on different surfaces (gold, silver, platinum, copper, mercury and glass), chemisorption of thiols on gold is a common and simple procedure to immobilize probes on a surface. DNA functionalized gold nanoparticles have since become widely used building blocks in key nucleic acid based assembly strategies and serve as unique probes for recognizing specific sequences in DNA segments [Storhoff, J. J., Elghanian, R., Mucic, R. C., Mirkin, C. A., and Letsinger, R. L. J. Am. Chem. Soc. 1998 120, 1959] as a building blocks for assembling novel structures and materials [Mucic, R. C., Storhoff, J. J., Mirkin, C. A., Letsinger, R. L. J. Am. Chem. Soc. 1998 120, 12674] and bio diagnostics and nano technology based therapeutics [Merkins, C. A., Letsinger, R. L., Mucic, R. C., Storhoff, J. J. Nature, 1996, 382, 607; Hurst, S. J., Hill, H. D., Mirkin, C. A. J. Am. Chem. Soc. 2008, 130, 12192]. It's been proven that formation of these monolayers is influenced by several factors such as temperature, solvent, buffer concentration, chain length of the adsorbate, cleanliness of the substrate, and rate of reaction with the surface and the reversibility of adsorption of the components of the monolayer. These applications depend on the reversible association of gold and sulfur bond between the attached oligonucleotide and nano particle.

The oligonucleotides attached with single thiol group are unstable during the washing steps and formation of stable attachment of oligonucleotides is very important property for its success in applications such as for DNA chip technology. The covalent bond between gold and sulfur is in the order of magnitude from 30 to 40 K cal/mol, which is relatively weak in order to anchor a biopolymer onto a surface. [Dubois L. H., Zegarski B. R., Nuzzo R. G. Proc. Nati. Acad. Sci. USA 1987 84 4739; Liepold, P., Kratzmüller, T., Persike, N., Bandilla, M., Hinz, M., Wieder, 15H., Hillebrandt, H., Ferrer, E., Hartwich, G. Anal Bioanal Chem, 2008, 391, 1759-1772]. It has been reported that oligonucleotides that are conjugated with mono functional thiol group are slowly lost at higher temperatures and also in the presence of high salt concentration buffers [Li, Z., Jin, R., Mirkin, C. A., Letsinger, R. L. *Nucleic Acids Res.* 2002, 30, 1558]. The stability studies by Letsinger et. al. on SAMs of oligonucleotides that are conjugated to gold surface by mono thiol group revealed that these are completely displaced by treating with the buffers containing DTT [Letsinger, R. L., Elghanian, R., Viswanadham, G., Mirkin, C. A. *Bioconj. Chem.* 2000, 11, 289]. This feature limits applications of these probes in solutions containing thiols such as a PCR solution that has DTT as a stabilizer for the polymerase enzyme.

So there is strong need to develop novel disulfide compounds that are capable of forming stable SAMs of oligonucleotides for wider biological applications. One can anticipate that stability of mono layers could be increased by multiple numbers of gold-sulfur bonds per oligonucleotides. There have been few reports [Letsinger, R. L., Elghanian, R., Viswanadham, G., Mirkin, C. A. *Bioconj. Chem.* 2000, 11, 289-291; Hartwich, G., Frischmann, P., Ferrer, E., U.S. Pat. No. 7,601,848, 2002; Seliger, H., Prokein, T. U.S. Patent No 2005/0059728, 2004] that has introduced novel thiol modifiers which can generate multiple thiol groups per oligonucleotide. Its been proved that SAMs produced by these modifications are much more stable than corresponding SAMs generated by mono thiol modifier in buffers containing DTT [Letsinger, R. L., Elghanian, R., Viswanadham, G., Mirkin, C. A. *Bioconj. Chem.* 2000, 11, 289]. However the DMT group attached to the side chain in the disclosed art is attached to a secondary hydroxyl, which can effect the quality of oligonucleotides attached to solid surfaces. The present invention utilizes nucleoside 5'-DMT group for oligonucleotide growth band thereby synthesis of high quality dithiolane oligonucleotides.

Chart 1:

Chemical structures of N2-Guanosine (O6-protected) functionalized dithiolane phosphoramidites 1, solid supports 2 and previously disclosed dithiolane phosphoramidites 3 and their solid supports 4.

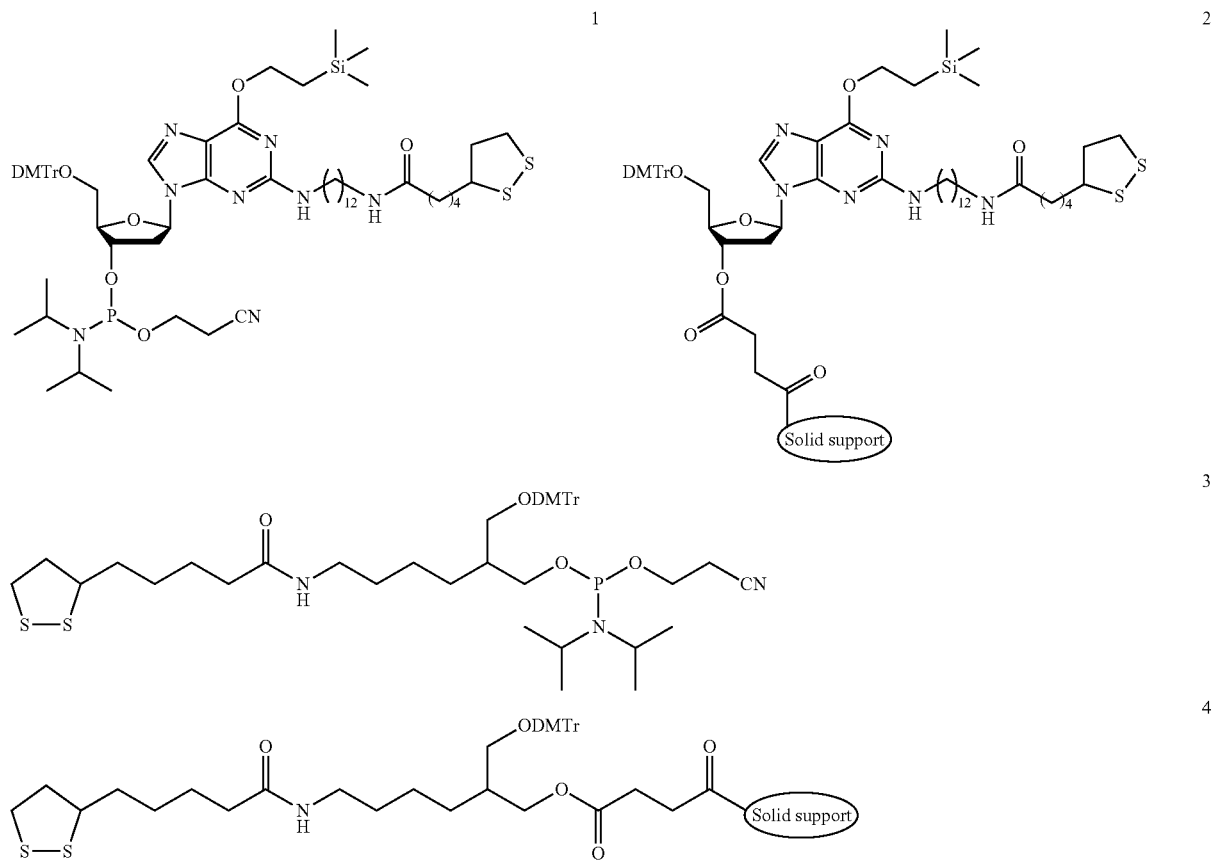

Previously, we have described five membered disulfide (dithiolane) based anchoring group 3 (Chart 1) for the introduction of two thiol groups [Srivastava, S. C., Thatikondra, S. K., Srivastav, S. K., Shukla, P. K., Srivastava, A., U.S. Provisional Application is 61/795,851, filed Oct. 27, 2012; U.S. Non-Provisional Application Ser. No. 14/065,385, filed Oct. 28, 2013.]. This dithiolane modification offered primary hydroxyl group to attach DMT group for the purpose of oligonucleotide synthesis, offers high quality oligonucleotide, and can potentially afford gold-oligonucleotide conjugates that exhibit greater stability.

REFERENCES

Cao, H., Yong, J., Yinsheng W. *Jour. of the Am. Chem. Soc.* 2007, 129, 12123-12130.
Connolly, B. A., Rider, P. *Nucleic Acids Res.* 1985 13, 4485
Dubois L. H., Zegarski B. R., Nuzzo R. G. *Proc. Nati. Acad. Sci. USA* 1987 84 4739-4742.
Hartwich, G., Frischmann, P., Ferrer, E., U.S. Pat. No. 7,601,848, filed Dec. 21, 2002.
Hurst, S. J., Hill, H. D., Mirkin, C. A. *J. Am. Chem. Soc.* 2008, 130, 12192.

Jones, D. S., Hachmann, J. P., Conrad, M. J., Coutts, S., Livingston, D. A. U.S. Pat. No. 5,391,785, Date filed Feb. 21, 1995.
Letsinger, R. L., Elghanian, R., Viswanadham, G., Mirkin, C. A. *Bioconj. Chem.* 2000, 11, 15 289-291.
Li, Z., Jin, R., Mirkin, C. A., Letsinger, R. L. *Nucleic Acids Res.* 2002, 30, 1558-62.
Liepold, P., Kratzmüller, T., Persike, N., Bandilla, M., Hinz, M., Wieder, H., Hillebrandt, H., Ferrer, E., Hartwich, G. *Anal Bioanal Chem,* 2008, 391, 1759-1772.
Merkins, C. A., Letsinger, R. L., Mucic, R. C., Storhoff, J. J. *Nature,* 1996, 382, 607. 20.
Mucic, R. C., Storhoff, J. J., Mirkin, C. A., Letsinger, R. L. *J. Am. Chem. Soc.* 1998 120, 12674-12675.
Nuzzo, R. G., Allara, D. L. *Jour. Am. Chem. Soc.* 1983, 105, 4481.
Seliger, H., Prokein, T. U.S. Patent No 2005/0059728 A1, filed Aug. 26, 2004 25.
Srivastava, S. C.; Thatikonda, S. K.; Srivastav, S. K. Shukla, P. U.S. Patent Application No. 2012/000103, 2012.
Srivastava, S. C., Thatikonda, S. K., Srivastav, S., Srivastava, A. The Ser. No. for the provisional application is 61/795,851, its filing date is Oct. 27, 2012.
Storhoff, J. J., Elghanian, R., Mucic, R. C., Mirkin, C. A., and Letsinger, R. L. *J. Am. Chem. Soc.* 1998 120, 1959-1964.

SUMMARY OF INVENTION

A phosphoramidite derivative of structure 1 and solid support of structure 2

Structure 1

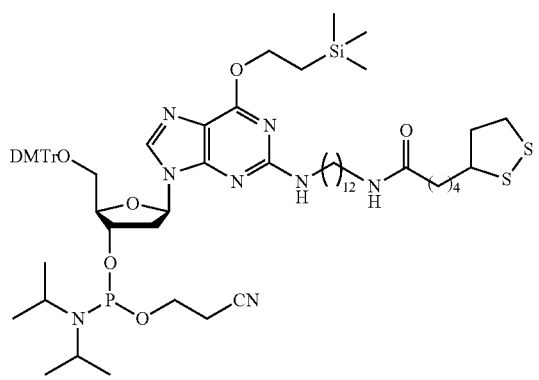

Structure 2

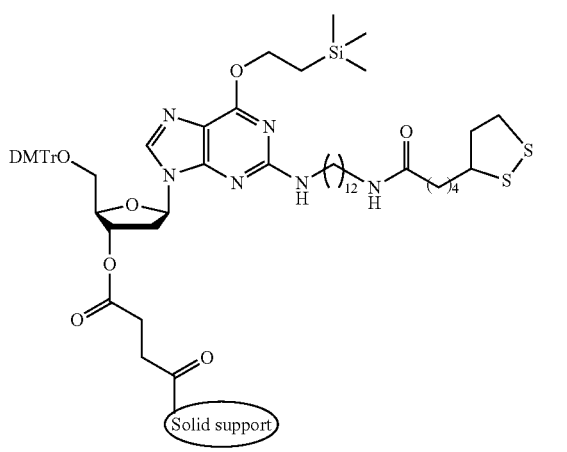

A C5-dithiolane functionalized pyrimidine nucleoside as described in the structure 3, 4.

Structure 3

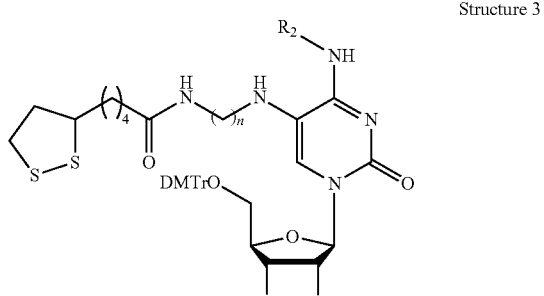

Structure 4

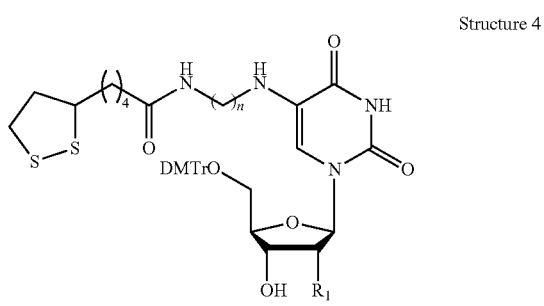

Where
$R_1$ = H, OH, F, O alkyl
$R_2$ = Ac, Bz
n = 1-20 carbon atoms

A C8-dithiolane functionalized purine nucleoside as described in the structure 5, 6.

Structure 5

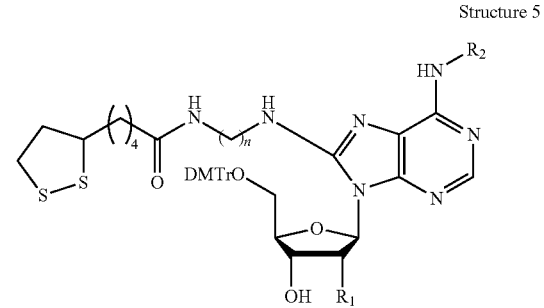

Structure 6

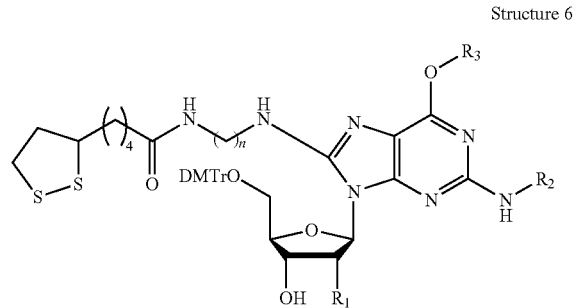

Where
$R_1$ = H, OH, F, O alkyl
$R_2$ = Ac, Bz, DMF
$R_3$ = Cyanoethyl, Ethyltrimethylsilyl
n = 1-20 carbon atoms A 2'-O-dithiolane functionalized pyrimidine nucleoside as described in the structure 7, 8.

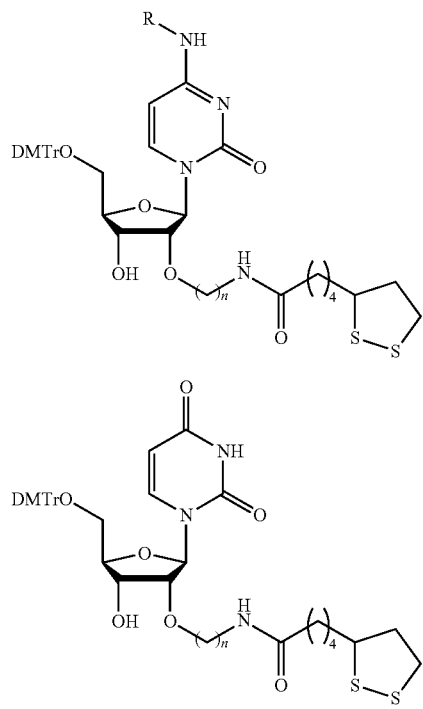

Where
R = Ac, Bz, DMF (dimethylformamidine)
n = 1-20

A 2'-O-dithiolane functionalized purine nucleoside as described in the structure 9, 10.

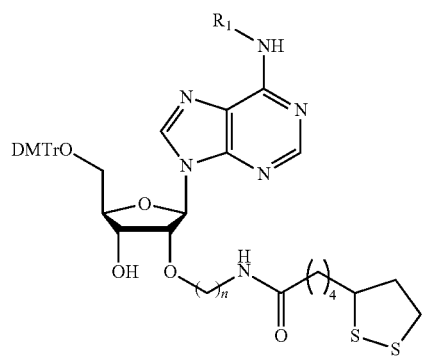

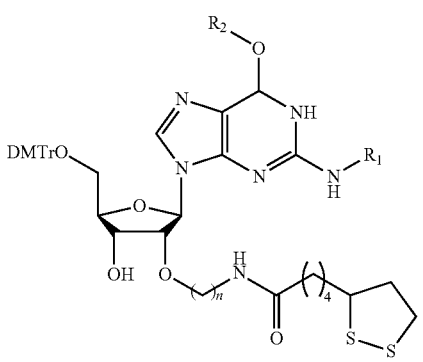

Where
R₁ = Bz, Ac, and DMA
R₂ = Ethyltrimethylsilyl, Cyanoethyl
n = 1-20 carbon atoms A C5-Dithiolane functionalized pyrimidine nucleoside amidites as described in the structure 11, 12.

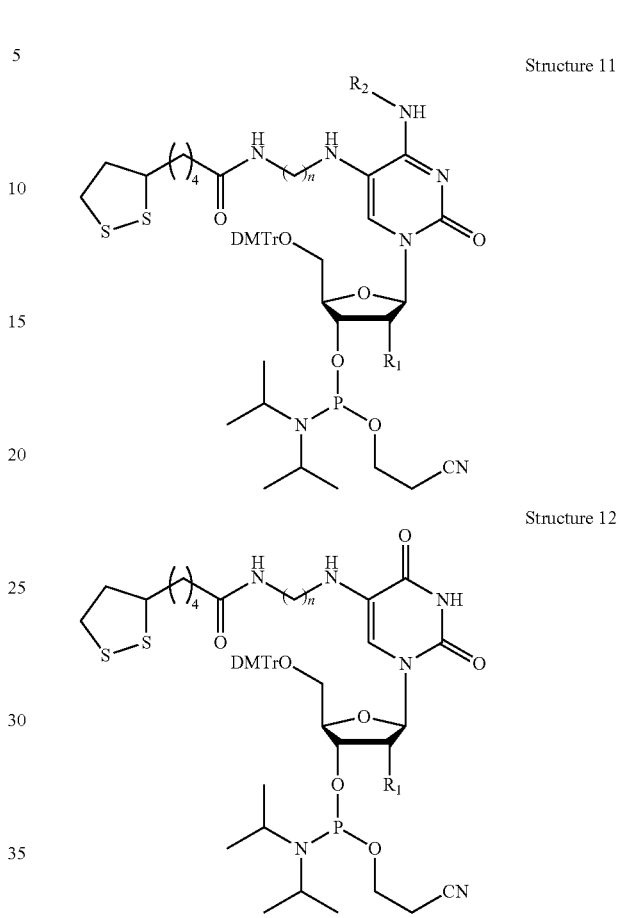

Where
$R_1$ = H, OH, F, Oalkyl
$R_2$ = Ac, Bz
n = 1-20 carbon atoms

A C8-dithiolane functionalized purine nucleoside amidites as described in the structure 13, 14.

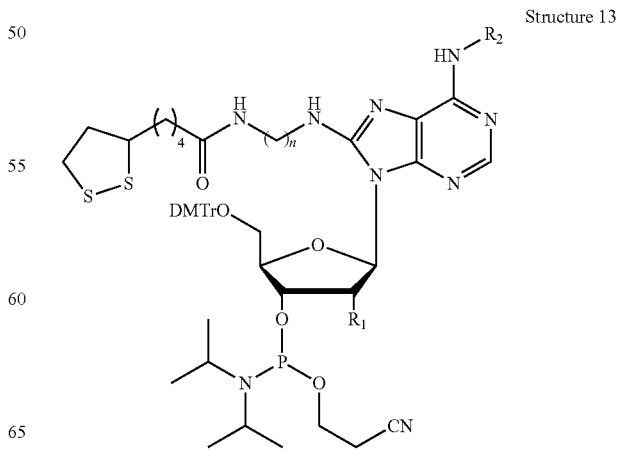

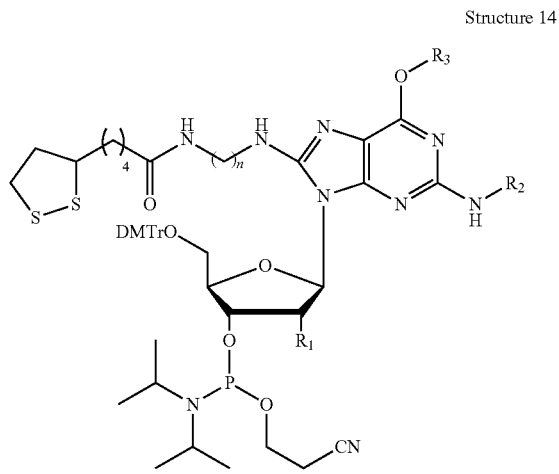

Structure 14

Where
R₁ = H, OH, F, Oalkly
R₂ = Ac, Bz, DMF
R₃ = Cyanoethyl, Ethyltrimethylsilyl
n = 1-20 carbon atoms A 2'-O-dithiolane functionalized pyrimidine nucleoside amidites as described in the structure 15, 16.

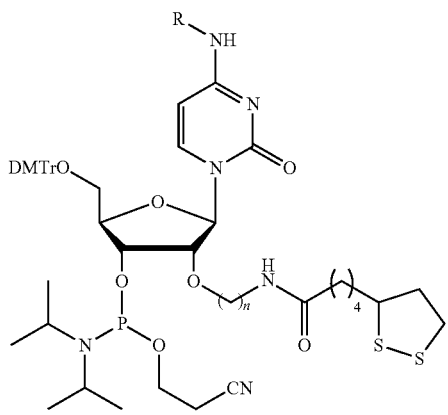

Structure 15

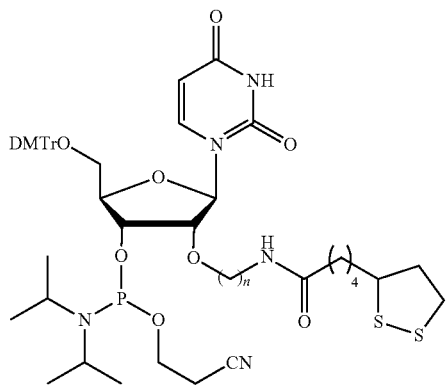

Structure 16

Where
R = Ac, Bz, DMF (dimethylformamidine)
n = 1-20

A 2'-O-dithiolane functionalized purine nucleoside amidites as described in the structure 17, 18.

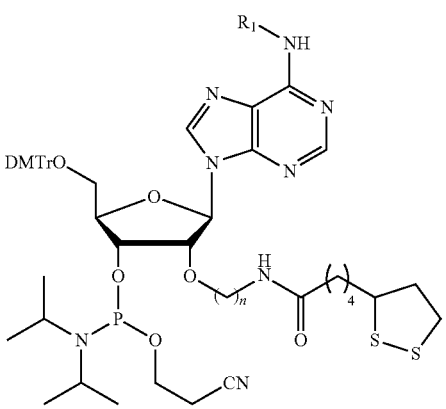

Structure 17

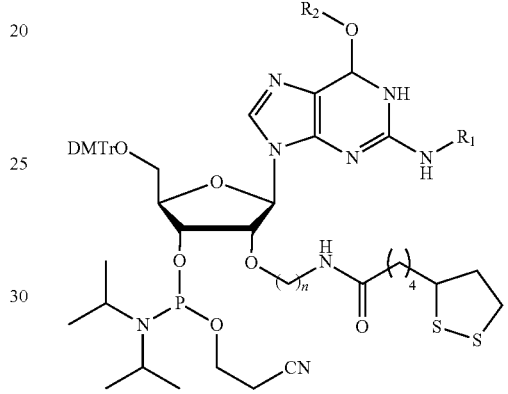

Structure 18

Where
R₁ = Bz, Ac and DMA
R₂ = Ethyltrimethylsilyl, Cyanoethyl
n = 1-20 carbon atoms A C-5 functionalized pyrimidine and C8-functionalized purine succinates as shown in the structure 19-22

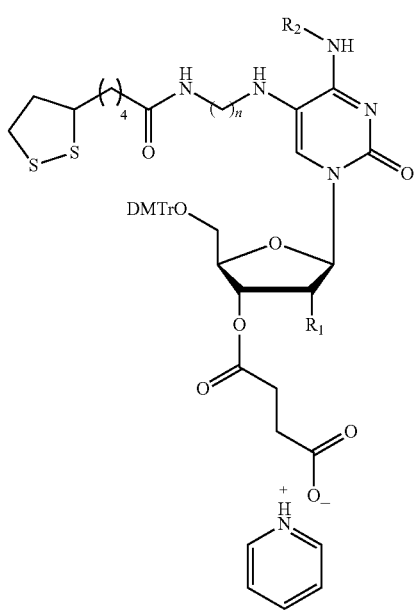

Structure 19

Structure 20
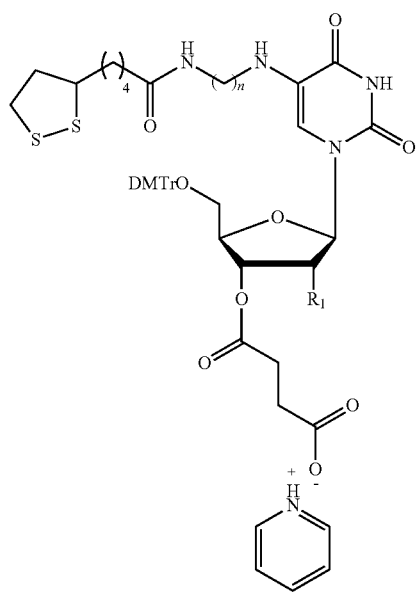
Structure 22
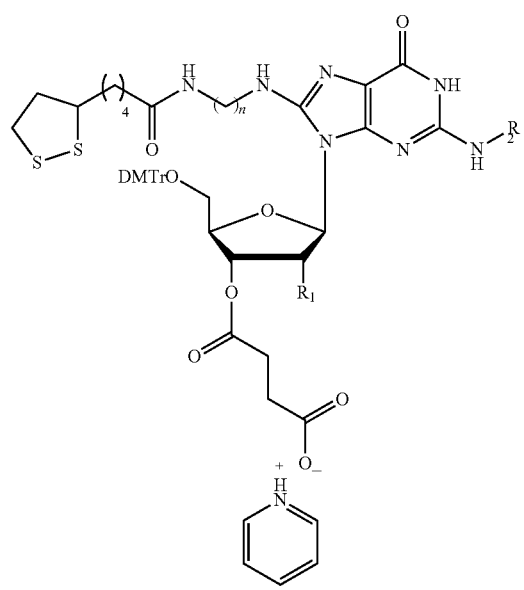
Where
R$_1$ = H, OH, F, Oalkly
R$_2$ = Nucleobase protecting groups that are compatible with oligonucleotide synthesis
n = 1-20 carbon atoms
A 2'-O-functionalized pyrimidine and purine succinates as shown in the structure 23-26.
Structure 21
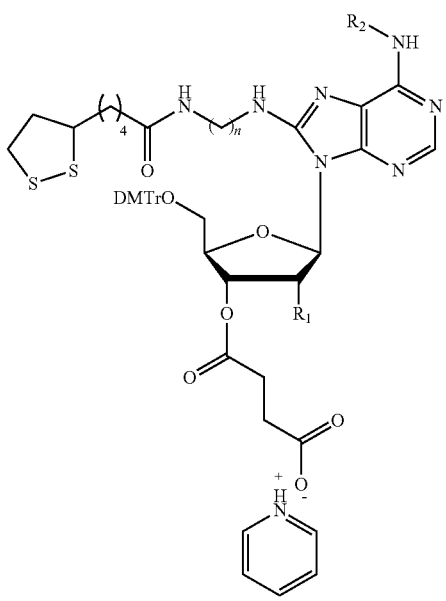
Structure 23
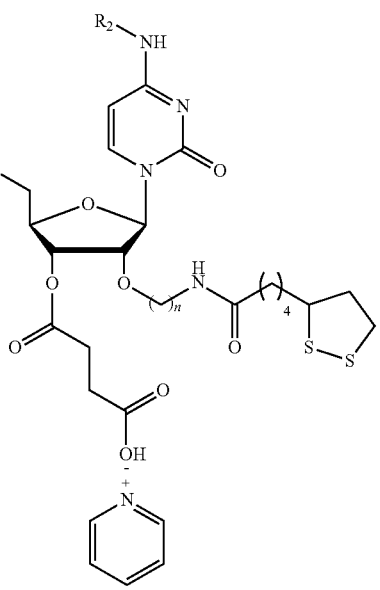

Structure 24
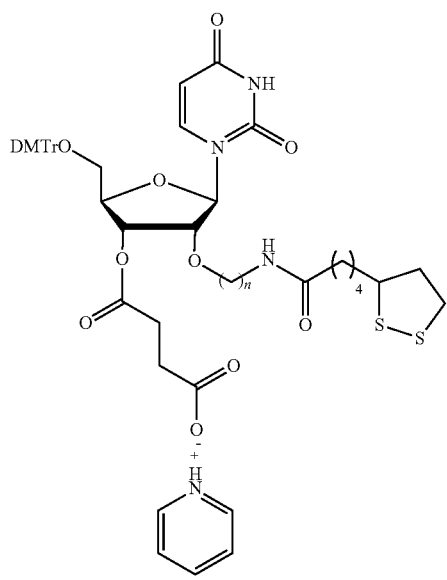
Structure 26
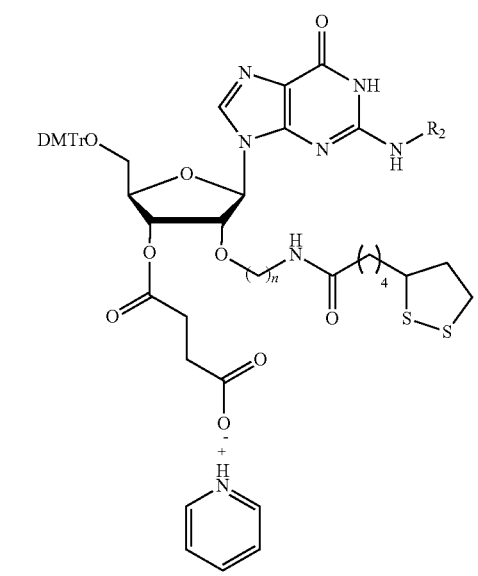
Where
$R_1$ = H, OH, F, Oalkyl
$R_2$ = Bz Ac, DMF, DMA
n = 1-20 carbon atoms
A C5 functionalized pyrimidine and purine solid supports as shown in the structure 27-30.
Structure 27
Structure 28
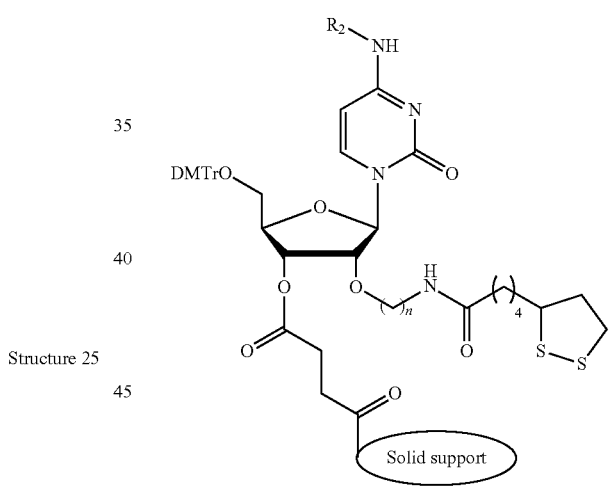
Structure 25
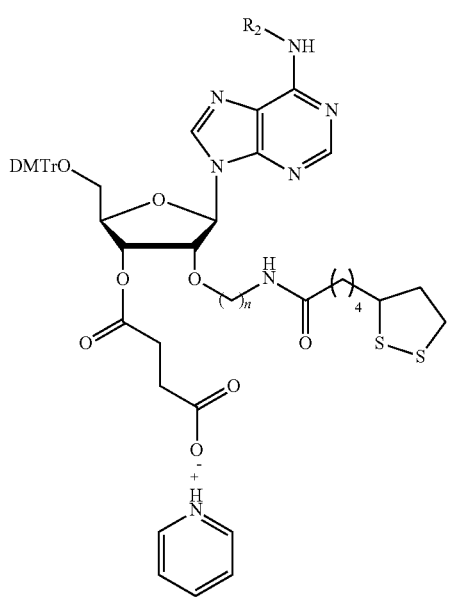

-continued

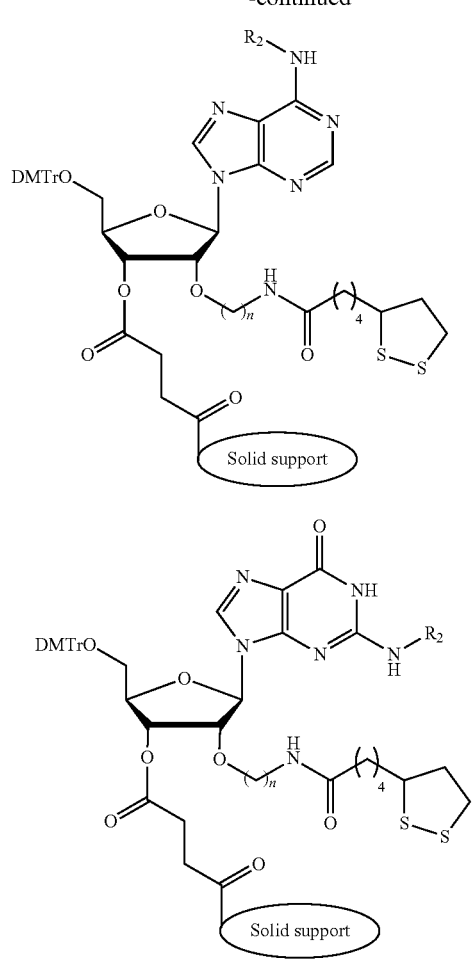

Structure 29

Structure 30

Where
R₁ = H, OH, F, Oalkyl
R₂ = Bz Ac, DMF, DMA
n = 1-20 carbon atoms

An oligoribonucleotide or an oligodeoxyribonucleotide containing with C5 and 2'-O-dithiolane functionalized Structure 1 to Structure 30 as described above.

A conjugate of the oligoribonucleotide or the oligodeoxyribonucleotide from as described above with solid supports such as gold, quantum dots as illustrated in FIG. 14.

The thiol modified oligonucleotides have vast number of applications in the field of nucleic acid chemistry such as it enables covalent attachment of a variety of ligands and also has an ability to form relatively stronger bond with gold surface. Hence, oligonucleotides with thiol groups can chemisorb onto gold surface and generate self-assembled mono layers (SAMs). DNA functionalized gold nanoparticles have become widely used building blocks in key nucleic acid based assembly strategies and serve as unique probes for recognizing specific sequences in DNA segments, as building blocks for assembling novel structures and materials, bio diagnostics and nano technology based therapeutics.

Even though thiol group forms relatively stronger bond with elemental gold (about 30-40 K cal/mole), it gets displaced at higher temperature, in high salt concentration buffers and in presence other thiols. For many of applications with these conjugates strong binding of the oligonucleotides to the gold nano particles is required. However to circumvent displacement of thiol, a few cyclic disulfide modifiers that can introduce multiple thiol groups have been introduced in the prior art. Their stability studies revealed that these multi-thiol functionalized oligonucleotides form relatively more stable SAMs compared to the corresponding mono-thiol derivatives.

In the present invention, we describe the design and efficient synthesis of cyclic dithiolane functionalized phosphoramidite derivative 1 (Chart 1) and corresponding dithiolane succinyl solid supports 2 (Chart 1). Previously we have described five membered disulfide (dithiolane) based anchoring group 3 and 4 (Chart 1) for the introduction of two thiol groups [Srivastava, S. C., Thatikonda, S. K., Srivastav, S. K., Shukla, P. K. Srivastava, A. U.S. Provisional Application is 61/795,851, filed Oct. 27, 2012; U.S. Non-Provisional application Ser. No. 14/065,385, filed Oct. 28, 2013]. This dithiolane modification is simple to synthesize, is broadly useful, and can potentially afford gold-oligonucleotide conjugates that exhibit greater stability. The task of the present invention is to extend this dithiolane technology further into nucleosides. In addition to the synthesized dithiolane functionalized derivatives 1 (Chart 1), we envisioned various other functionalized derivatives compounds from Schemes 1 to 8. Conjugation of dithiolane moiety to the either nucleobase or to sugar part with linker arm should generate very interesting functionalized thiol oligonucleotides. The advantage of relatively long linker arm is that it allows clean formation of the monomers on the solid surfaces and keeps the self-assembled monomers in the optimum distance from the solid support. Pairs of oligonucleotide-gold nano-particle conjugates serve as unique probes for recognizing specific sequences in DNA segments, as building blocks for assembling novel structures, bio diagnostics and nano technology based therapeutics.

BRIEF DESCRIPTION OF DRAWINGS

FIG. 2: HPLC table peaks of the 2-(12-Aminododecanyl)-2'-deoxy-5'-O-(4,4'-Dimethoxytrityl)-O6-(2-trimethylsilylethyl)-Guanosine (54).

FIG. 6: HPLC table peaks of the 2'-Deoxy-5'-O-(4,4'-Dimethoxytrityl)-2-(12-(5-(1,2-dithiolan-3-yl)pentanamide)-dodecyl)-O6-(2-trimethylsilylethyl)-Guanosine (55).

FIG. 10: HPLC table peaks of the 3'-(2-Cyanoethyl diisopropylphosphoramidite)-2'-deoxy-5'-O-(4,4'-dimethoxytrityl)-2-(12-(5-(1,2-dithiolan-3-yl)pentanamide)-dodecyl)-O6-(2-trimethylsilylethyl)-Guanosine (1).

DETAILED DESCRIPTION OF THE INVENTION

Figure 1:
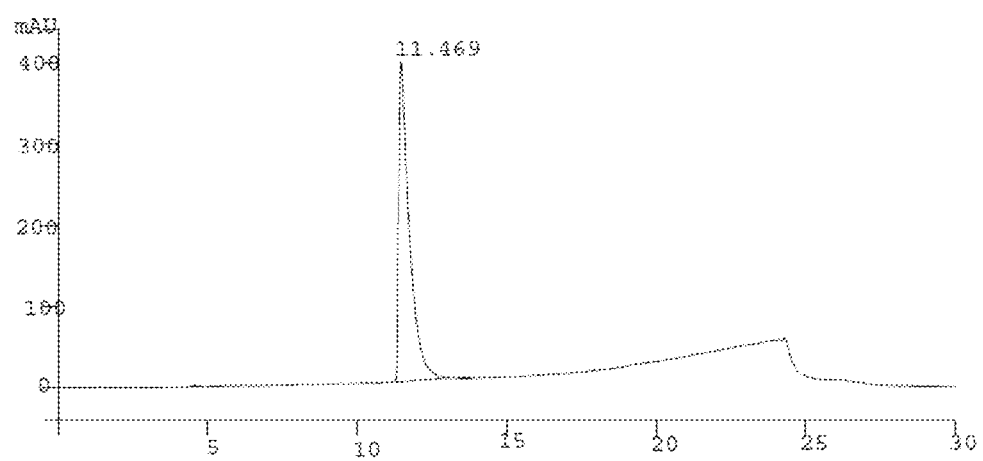
FIG. 1: HPLC purity analysis of the 2-(12-Aminododecanyl)-2'-deoxy-5'-O-(4,4'-Dimethoxytrityl)-O6-(2-trimethylsilylethyl)-Guanosine (54). Analytical purity of compounds was checked using a Varian Prostar HPLC equipped with ChromSep SS column (4.6×250 mm) 10 and ChromSep Guard-Column OmniSpher 5 C18. Mobile phase: A 0.1M Triethylammonium acetate (TEAA); B is CH3CN. Analysis was performed with the linear gradient of increase of B from 65 to 98% in 20 min. Peaks were detected by UV absorption at 254 nm.
Figure 3:
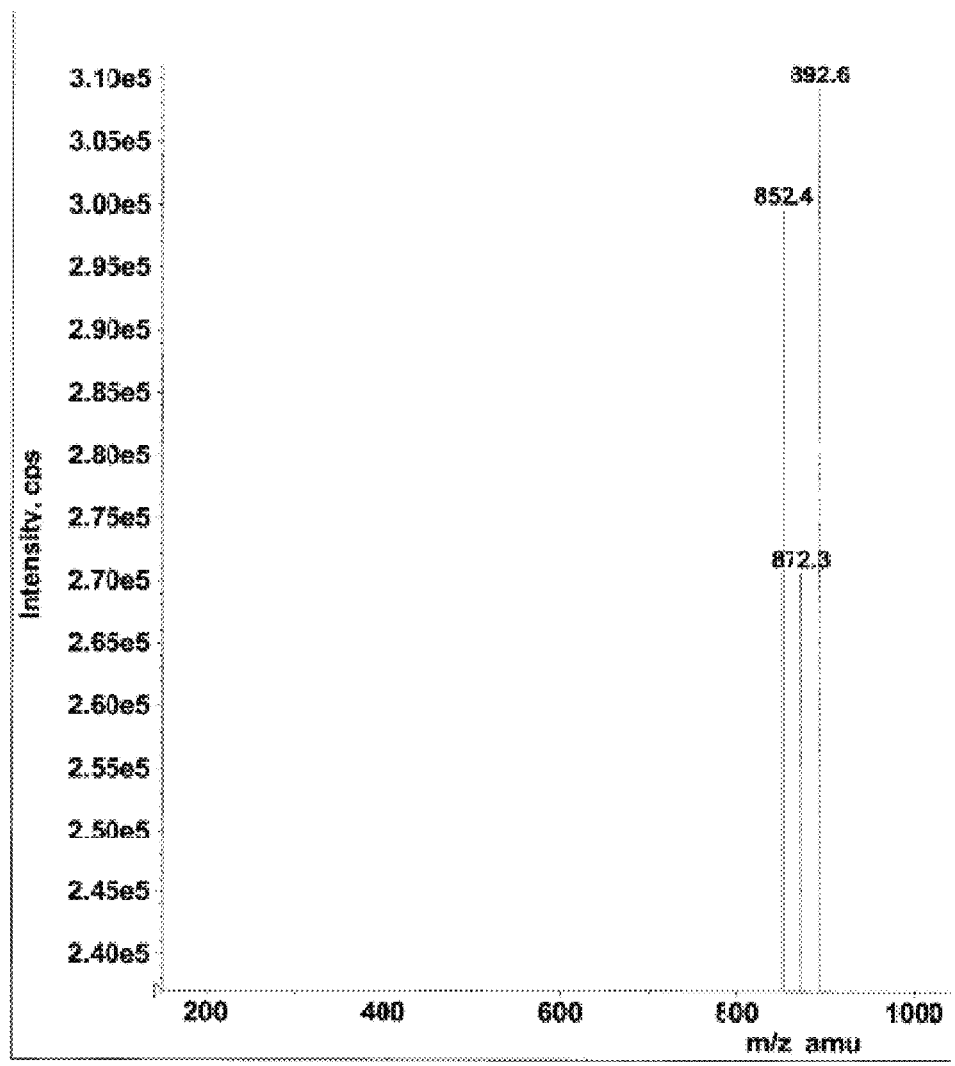
FIG. 3: ESI/MS spectra of the 2-(12-Aminododecanyl)-2'-deoxy-5'-O-(4,4'-Dimethoxytrityl)-O6-(2-trimethylsilylethyl)-Guanosine (54). MS m/z ($C_{48}H_{68}N_6O_6Si$) [M−H]⁻ 852.4, calcd 853.18. ESI/MS analysis was carried on Perkin Elmer 30 PE-SCIEX API-150 mass spectrometer.
Figure 4:
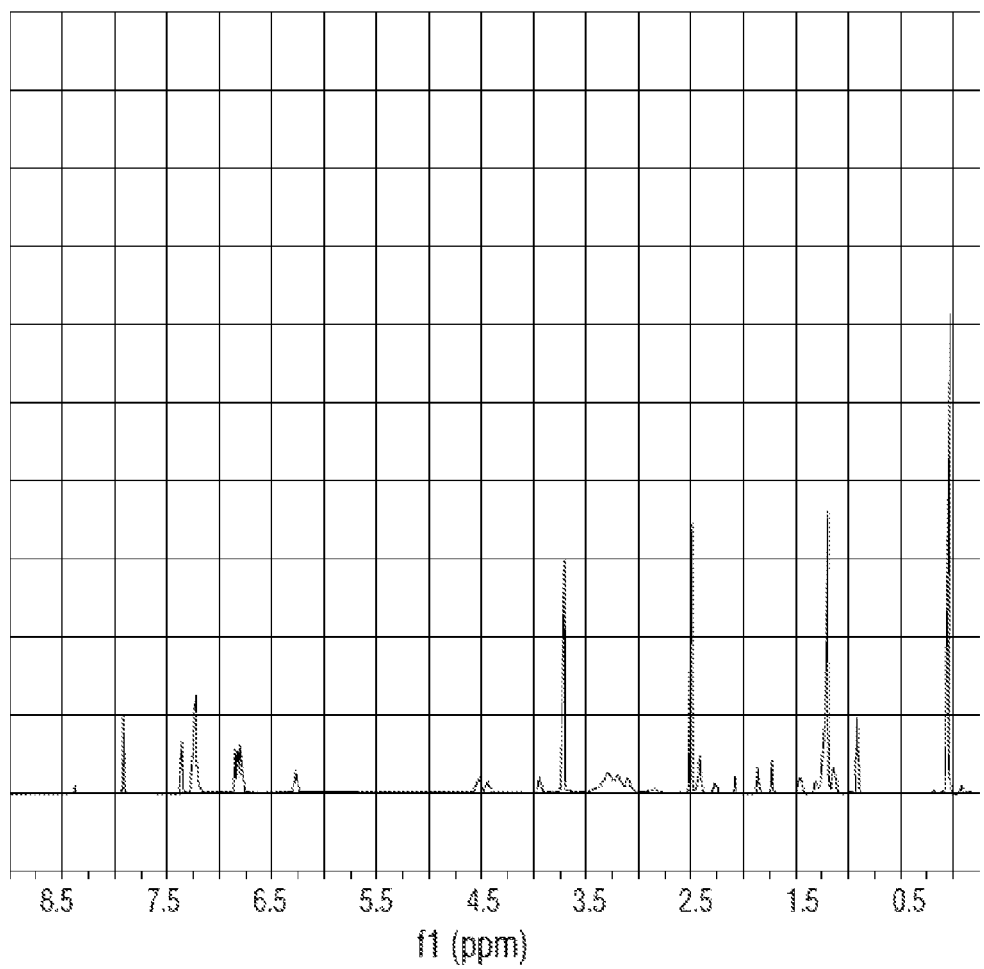
FIG. 4: ¹H NMR of 2-(12-Aminododecanyl)-2'-deoxy-5'-O-(4,4'-dimethoxytrityl)-O6-(2-trimethylsilylethyl)-Guanosine (54). ¹H NMR was recorded on [0001.] Bruker 500 MHz NMR spectrophotometer. Chemical shifts are calibrated with deuterated solvent CDCl3 (δ 7.26 ppm).
Figure 5:
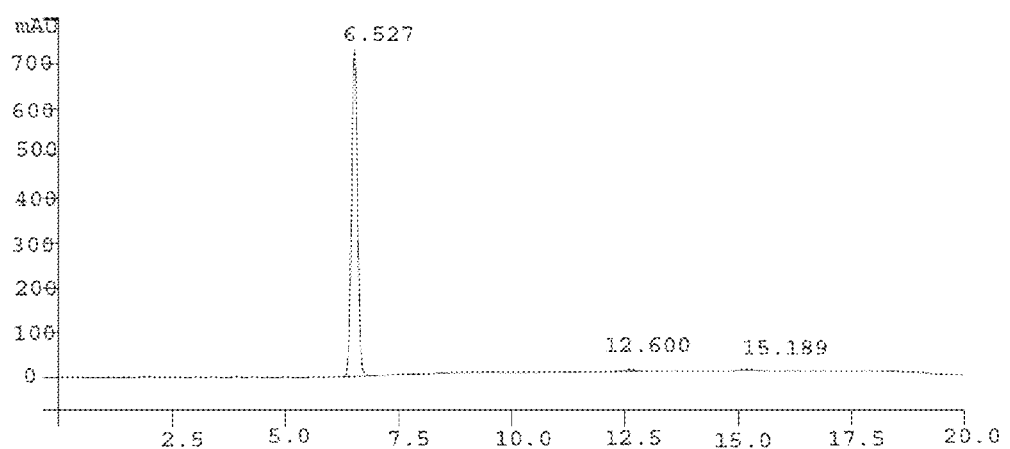
FIG. 5: HPLC purity analysis of the 2'-Deoxy-5'-O-(4,4'-Dimethoxytrityl)-2-(12-(5-(1,2-dithiolan-3-yl)pentanamide)-dodecyl)-O6-(2-trimethylsilylethyl)-Guanosine (55). Analytical purity of compounds was checked using a Varian Prostar HPLC equipped with ChromSep SS column (4.6× 250 mm) 10 and ChromSep Guard-Column OmniSpher C18. Mobile phase: A 0.1M Triethylammonium acetate (TEAA); B is CH3CN. Analysis was performed with the linear gradient of increase of B from 0 to 50% in 20 min. Peaks were detected by UV absorption at 254 nm.
Figure 7:
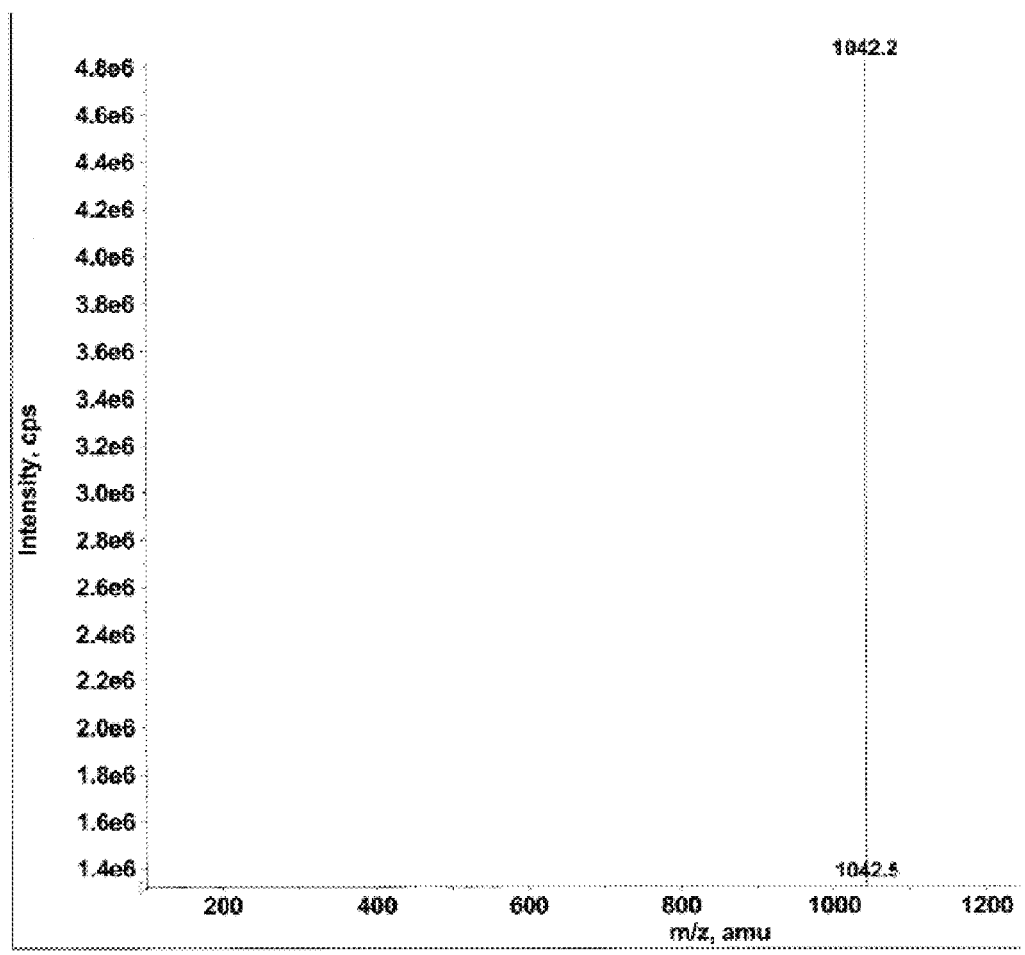
FIG. 7: ESI/MS spectra of the 2'-Deoxy-5'-O-(4,4'-Dimethoxytrityl)-2-(12-(5-(1,2-dithiolan-3-yl)pentanamide)-dodecyl)-O6-(2-trimethylsilylethyl)-Guanosine (55). MS m/z $C_{56}H_{80}N_6O_7S_2Si$ ([M+H]$^+$1042.2, calcd 1041.18). ESI/MS analysis was carried on Perkin Elmer 30 PE-SCIEX API-150 mass spectrometer.
Figure 8:
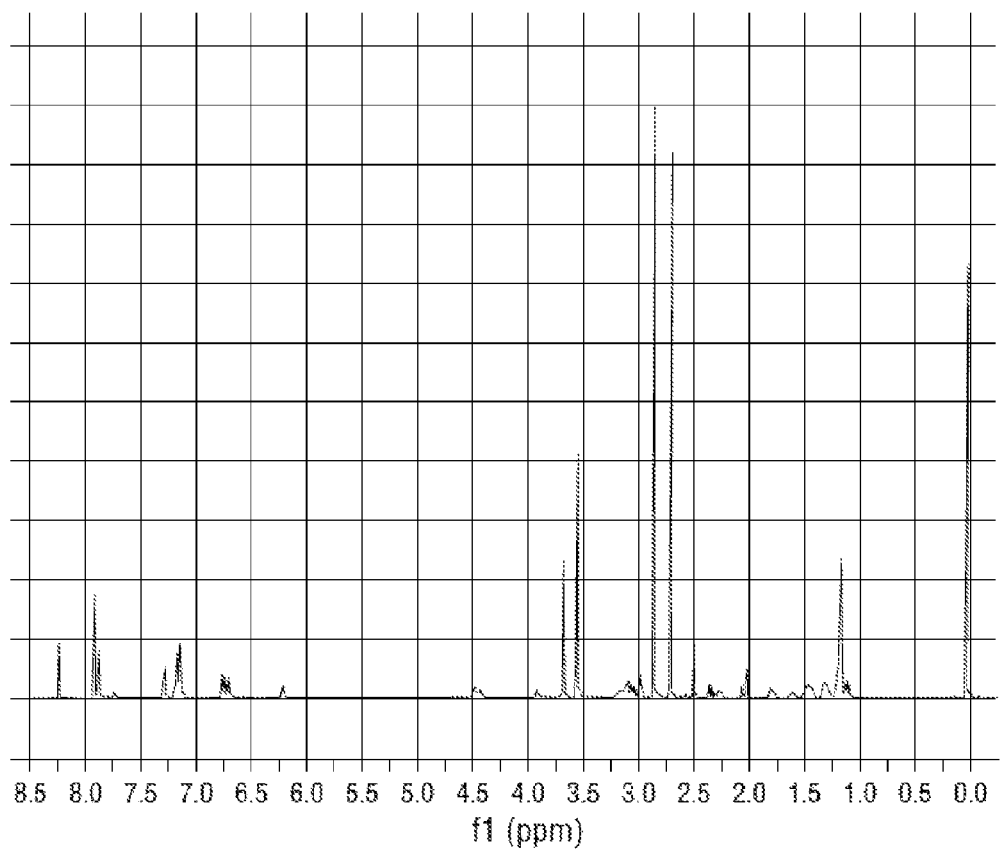
FIG. 8: $^1$H NMR of 2'-Deoxy-5'-O-(4,4'-Dimethoxytrityl)-2-(12-(5-(1,2-dithiolan-3-yl)pentanamide)-dodecyl)-O6-(2-trimethylsilylethyl)-Guanosine (55). $^1$H NMR was recorded on Bruker 500 MHz NMR spectrophotometer. Chemical shifts are calibrated with deuterated solvent CDCl3 (δ 7.26 ppm).
Figure 9:
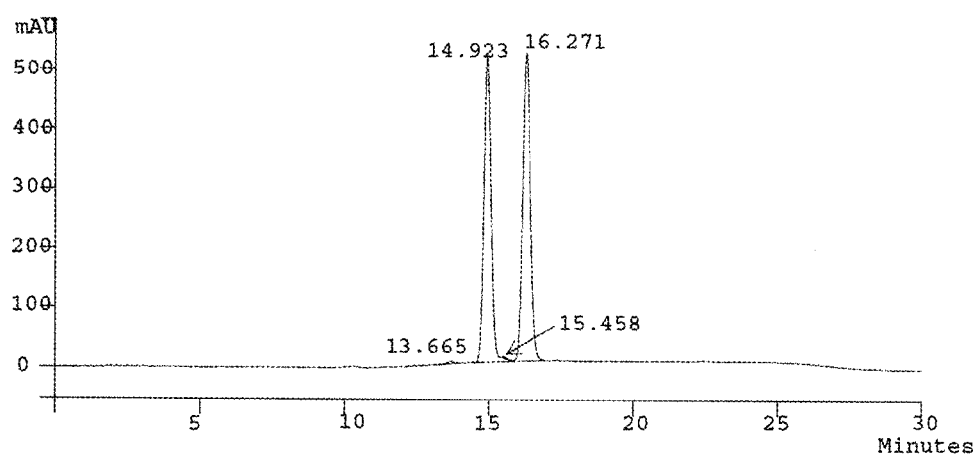
FIG. 9: HPLC purity analysis of the 3'-(2-Cyanoethyl diisopropylphosphoramidite)-2'-deoxy-5'-O-(4,4'-dimethoxytrityl)-2-(12-(5-(1,2-dithiolan-3-yl)pentanamide)-dodecyl)-O6-(2-trimethylsilylethyl)-Guanosine (1). Analytical purity of compounds was checked using a Varian Prostar HPLC equipped with ChromSep SS column (4.6×250 mm) 10 and ChromSep Guard-Column OmniSpher C18. Mobile phase: A 0.1M Triethylammonium acetate (TEAA); B is CH3CN. Analysis was performed with the linear gradient of increase of B from 0-30% in 20 min. Peaks were detected by UV absorption at 254 nm.
Figure 11:
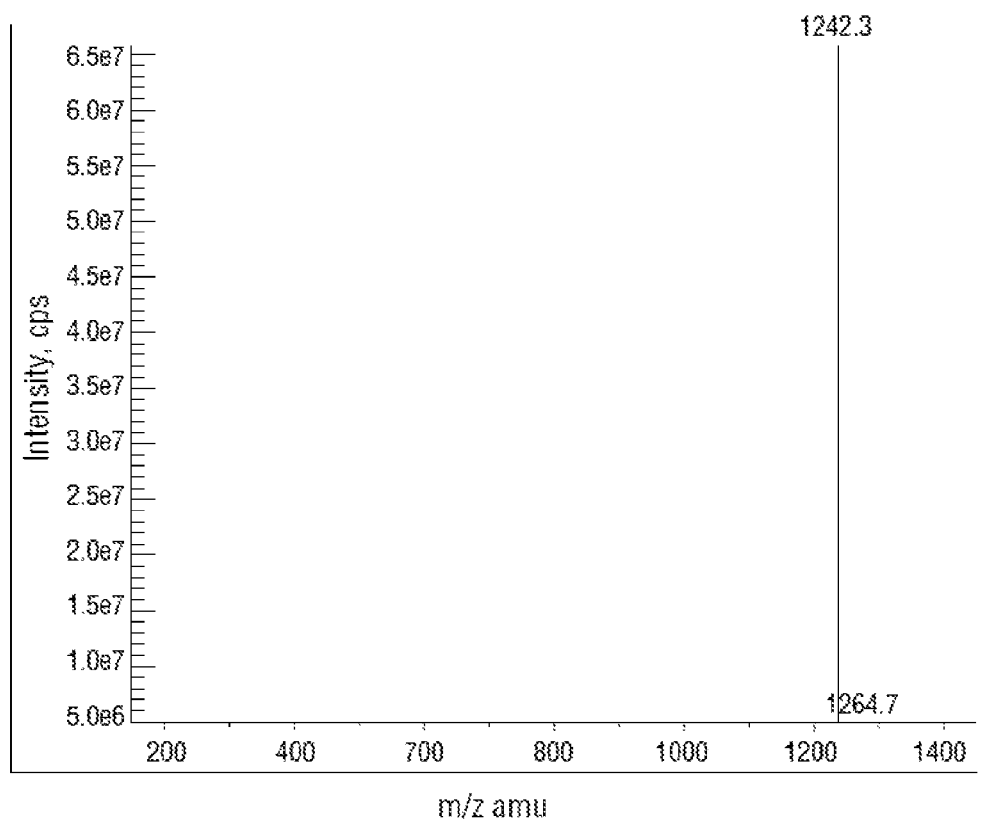
FIG. 11: ESI/MS spectra of the 3'-(2-Cyanoethyl diisopropylphosphoramidite)-2'-deoxy-5'-O-(4,4'-dimethoxytrityl)-2-(12-(5-(1,2-dithiolan-3-yl)pentanamide)-dodecyl)-O6-(2-trimethylsilylethyl)-Guanosine (1). MS m/z $C_{65}H_{97}N_8O_8PS_2Si$ [0002.] ([M+H]$^+$1242.3, calcd 1241.58). ESI/MS analysis was carried on Perkin Elmer 30 PE-SCIEX API-150 mass spectrometer.
Figure 12:
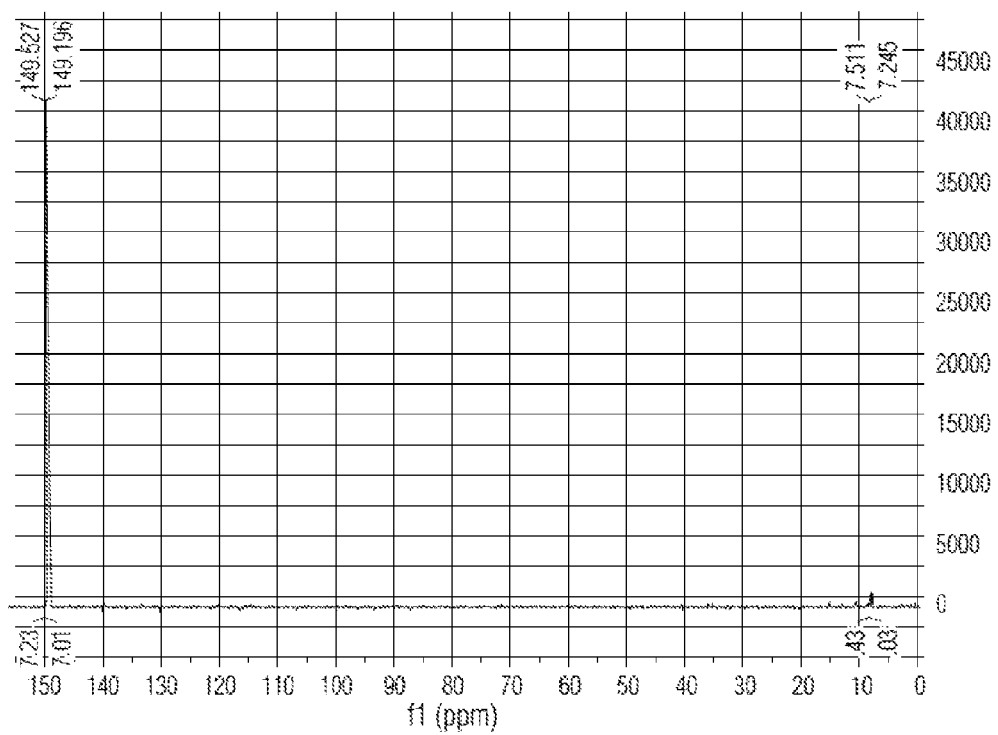
FIG. 12: $^{31}$P NMR spectra of 3'-(2-Cyanoethyl diisopropylphosphoramidite)-2'-deoxy-5'-O-(4,4'-dimethoxytrityl)-2-(12-(5-(1,2-dithiolan-3-yl)pentanamide)-dodecyl)-O6-(2-trimethylsilylethyl)-Guanosine (1). $^{31}$P NMR was recorded on Bruker 202 MHz NMR spectrophotometer. Solvent used for NMR analysis was $CDCl_3$.
Figure 13:
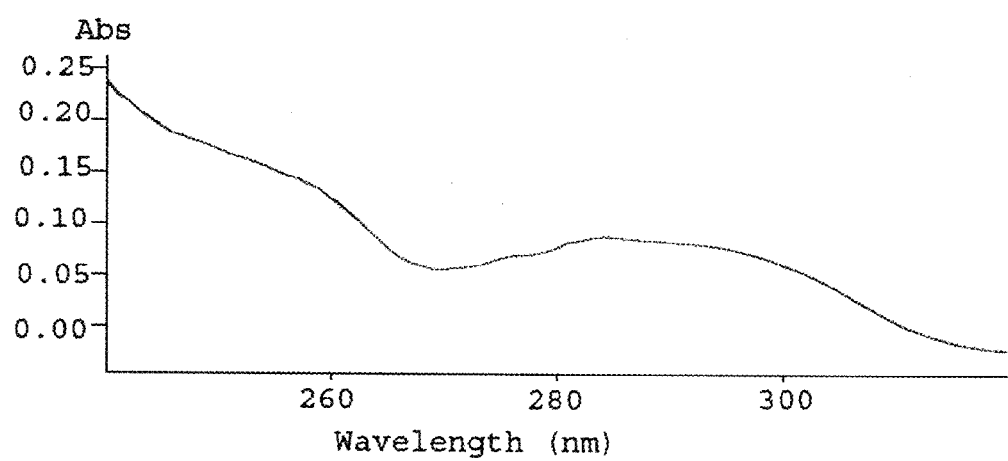
FIG. 13: UV absorption spectra of 3'-(2-Cyanoethyl diisopropylphosphoramidite)-2'-deoxy-5'-O-(4,4'-dimethoxytrityl)-2-(12-(5-(1,2-dithiolan-3-yl)pentanamide)-dodecyl)-O6-(2-trimethylsilylethyl)-Guanosine (1). UV absorption spectrum was recorded on Cary 50 Bio UV-Visible spectrophotometer in the range of 320 to 240 nm.

The present invention further extends this dithiolane technology further into nucleosides. Conjugation of dithiolane moiety to the either nucleobase or to sugar part with linker arm should generate very interesting functionalized thiol oligonucleotides. The advantage of relatively long linker arm is that it allows clean formation of the monomers on the solid surfaces and keeps the self-assembled monomers in the optimum distance from the solid support. Pairs of oligonucleotide-gold nano-particle conjugates serve as unique probes for recognizing specific sequences in DNA segments, as building blocks for assembling novel structures, bio diagnostics and nano technology based therapeutics.

One embodiment of the invention is directed to a nucleoside, comprising: a guanine, a 2'-deoxyribose, a dithiolane derivative at N2 of the guanine; and a phosphoramidite derivative at the 3'-O of the deoxyribose, or a solid support at the 3'-O of the deoxyribose, wherein the nucleoside is represented by Structure 1 or Structure 2:

Structure 1

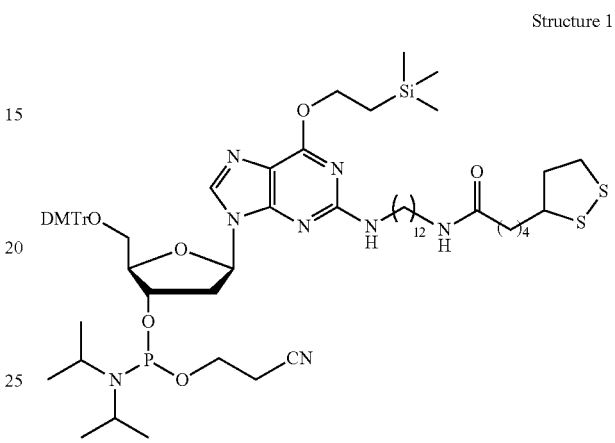

Structure 2

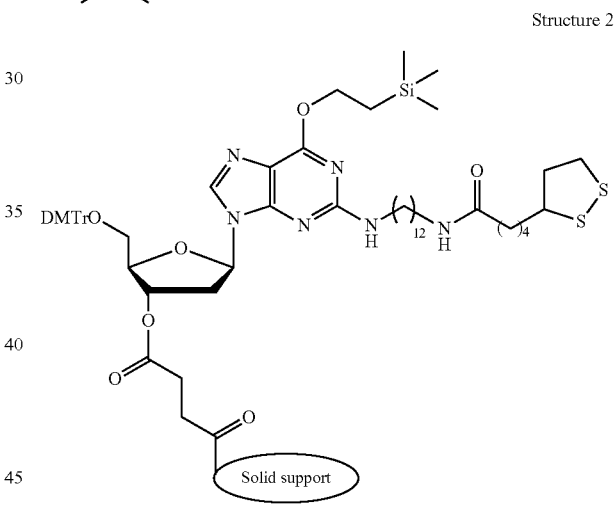

One embodiment of the invention is directed to a nucleoside, comprising: a pyrimidine; a ribose; and a dithiolane derivative at C5 of the pyrimidine, wherein the nucleoside is represented by Structure 3 or Structure 4:

Structure 3

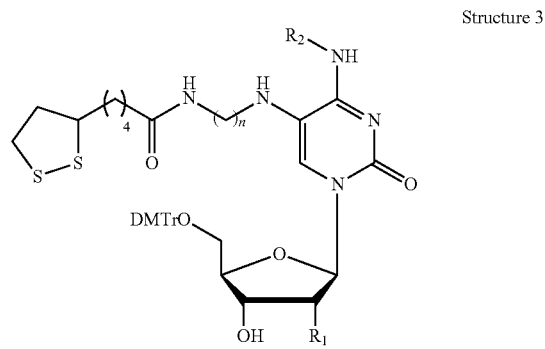

Structure 4

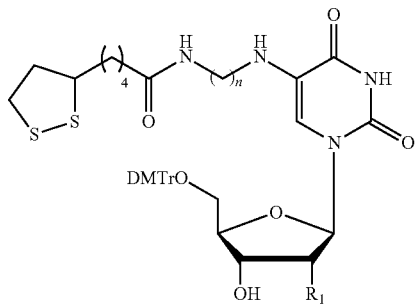

Where
R₁ = H, OH, F, Oalkyl
R₂ = Ac, Bz
n = 1-20 carbon atoms

One embodiment of the invention is directed to a nucleoside, comprising: a purine; a ribose; and a dithiolane derivative at C8 of the purine, wherein the nucleoside is represented by Structure 5 or Structure 6:

Structure 5

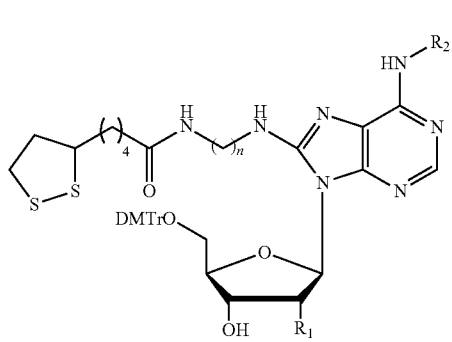

Structure 6

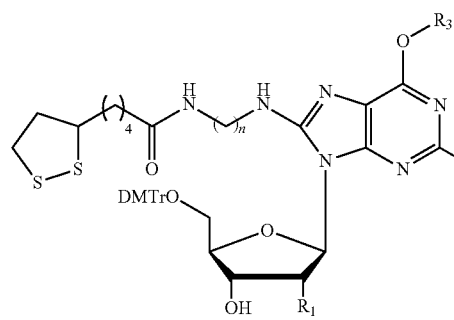

Where
R₁ = H, OH, F, Oalkly
R₂ = Ac, Bz, DMF
R₃ = Cyanoethyl, Ethyltrimethylsilyl
n = 1-20 carbon atoms One embodiment of the invention is directed to a nucleoside, comprising: a pyrimidine; a ribose; and a dithiolane derivative at 2'-O of the ribose, wherein the nucleoside is represented by Structure 7 or Structure 8:

Structure 7

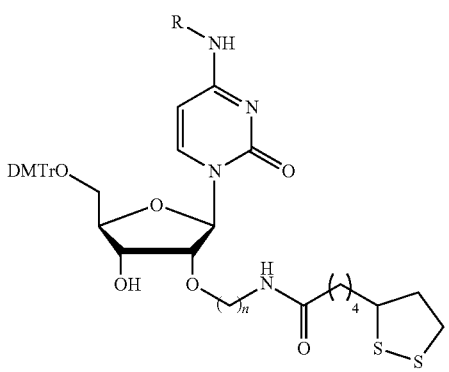

Structure 8

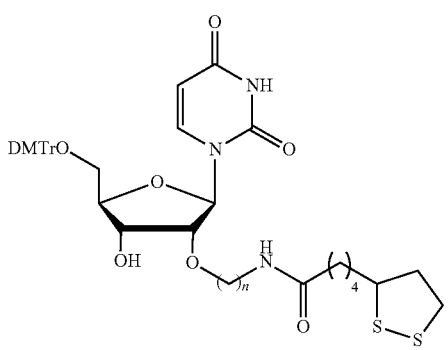

Where
R = Ac, Bz, DMF (dimethylformamidine)
n = 1-20

One embodiment of the invention is directed to a nucleoside, comprising: a purine; a ribose; and a dithiolane derivative at 2'O of the ribose, wherein the nucleoside is represented by Structure 9 or Structure 10:

Structure 9

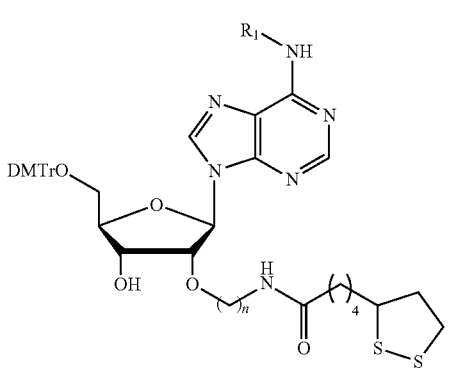

-continued

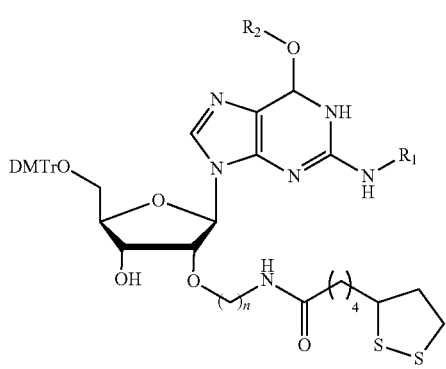

Structure 10

Where
R₁ = Bz, Ac and DMA
R₂ = Ethyltrimethylsilyl, Cyanoethyl
n = 1-20 carbon atoms One embodiment of the invention is directed to a nucleoside, comprising: a pyrimidine; a ribose; a dithiolane derivative at C5 of the pyrimidine; and a phosphoramidite group at 3'-O of the ribose, wherein the nucleoside is represented by Structure 11 or Structure 12:

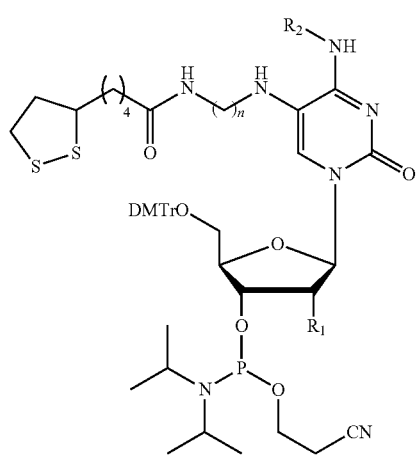

Structure 11

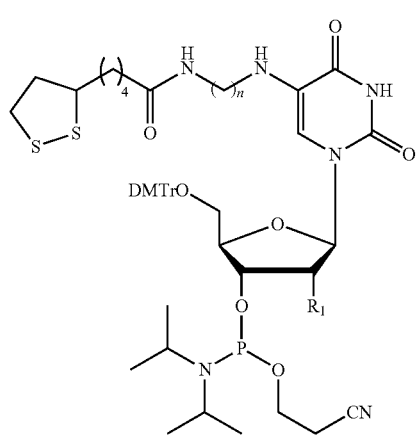

Structure 12

Where
R₁ = H, OH, F, Oalkyl
R₂ = Ac, Bz
n = 1-20 carbon atoms

One embodiment of the invention is directed to a nucleoside, comprising: a purine; a ribose; a dithiolane derivative at C8 of the purine; and a phosphoramidite group at 3'-O of the ribose, wherein the nucleoside is represented by Structure 13 or Structure 14:

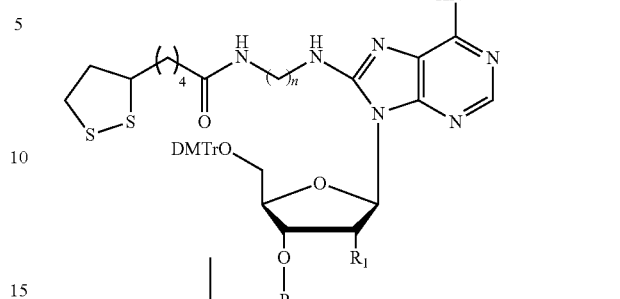

Structure 13

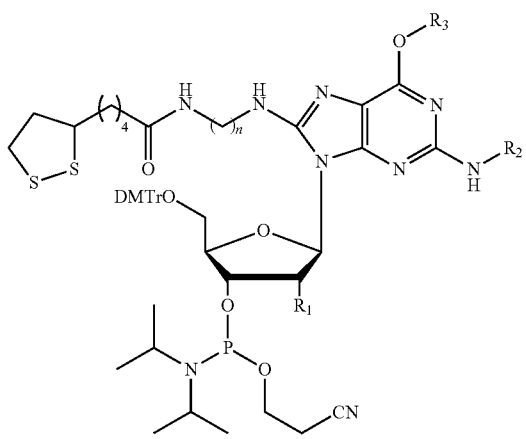

Structure 14

Where
R₁ = H, OH, F, Oalkly
R₂ = Ac, Bz, DMF
R₃ = Cyanoethyl, Ethyltrimethylsilyl
n = 1-20 carbon atoms One embodiment of the invention is directed to a nucleoside, comprising: a pyrimidine; a ribose; a dithiolane derivative at 2'-O of the ribose; and a phosphoramidite group at 3'-O of the ribose, wherein the nucleoside is represented by Structure 15 or Structure 16:

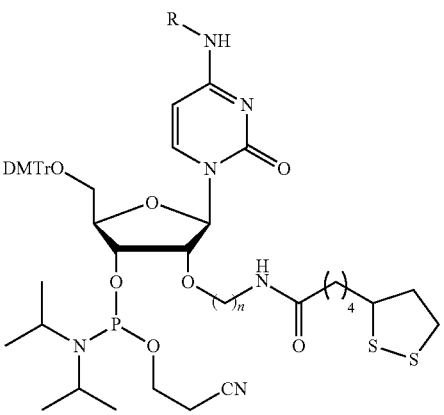

Structure 15

-continued

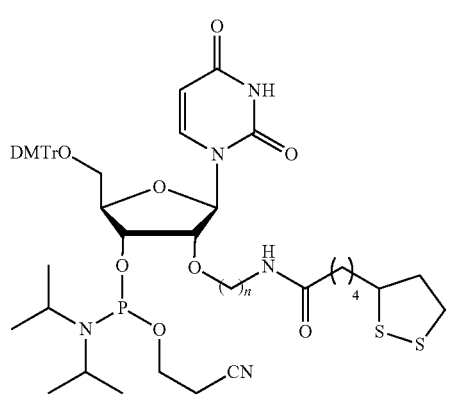

Structure 16

Where
R = Ac, Bz, DMF (dimethylformamidine)
n = 1-20

One embodiment of the invention is directed to a nucleoside, comprising: a purine; a ribose; a dithiolane derivative at 2'-O of the ribose; and a phosphoramidite group at 3'-O of the ribose, wherein the nucleoside is represented by Structure 17 or Structure 18:

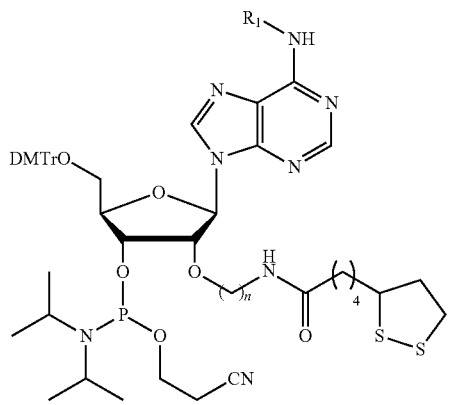

Structure 17

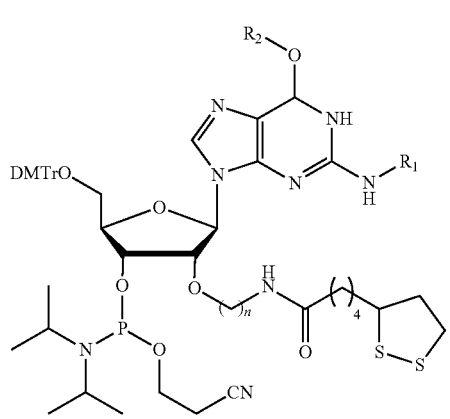

Structure 18

Where
$R_1$ = Bz, Ac and DMA
$R_2$ = Ethyltrimethylsilyl, Cyanoethyl
n = 1-20 carbon atoms One embodiment of the invention is directed to a nucleoside, comprising: a ribose; a succinate group at 3'-O of the ribose; and a pyrimidine or a purine, wherein the pyrimidine has a dithiolane derivative at C5 and the pyrimidine is represented by Structure 19 or Structure 20, the purine has a dithiolane derive at C8 and is represented by Structure 21 or Structure 22:

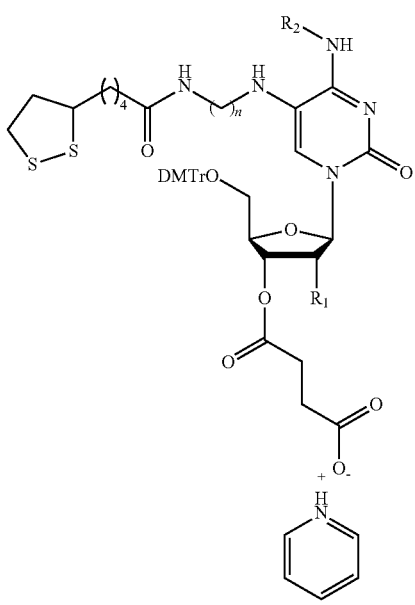

Structure 19

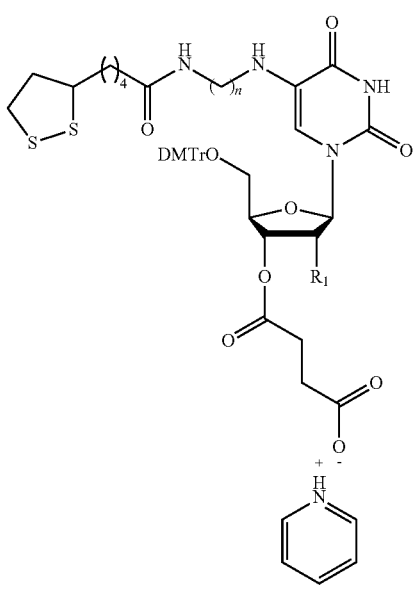

Structure 20

-continued

Structure 21
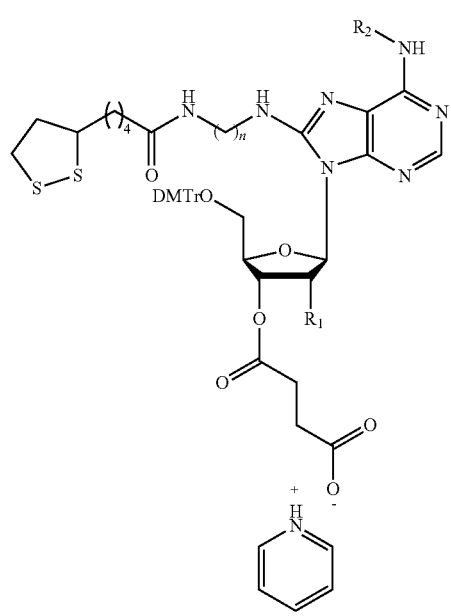

Structure 22
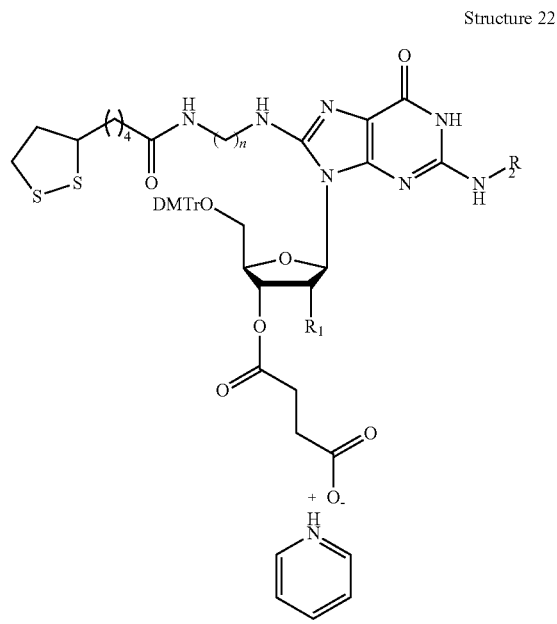

Where
R$_1$ = H, OH, F, Oalkyl
R$_2$ = Nucleobase protecting groups that are compatible with oligonuleoctides synthesis
n = 1-20 carbon atoms Structure 23
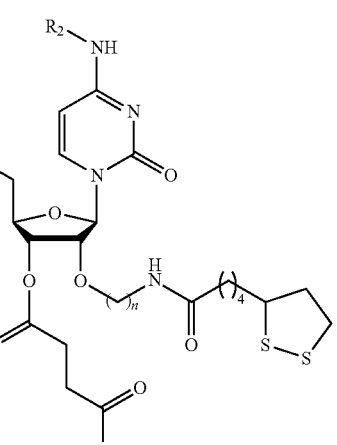

Structure 24
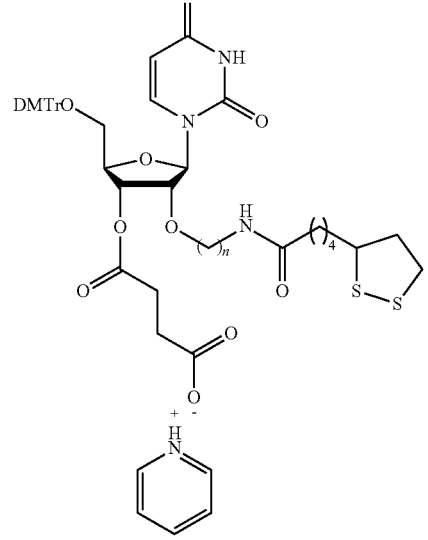

Structure 25
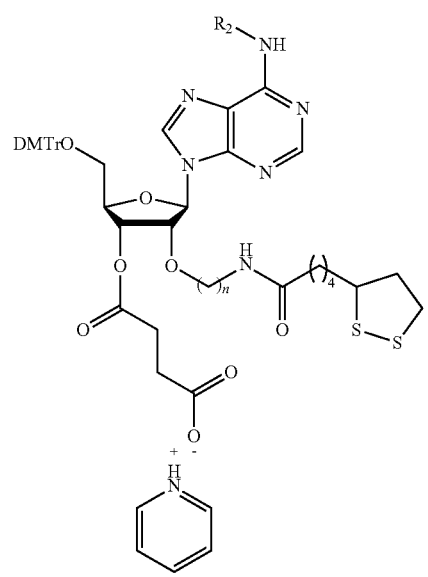

One embodiment of the invention is directed to a nucleoside, comprising: a nucleobase; a ribose; a dithiolane derivative at 2'-O of the ribose; and a succinate group at 3'-O of the ribose, wherein the nucleobase is a pyrimidine as represented by Structure 23 or Structure 24, or a purine as represented by Structure 25 or Structure 26:

Structure 26

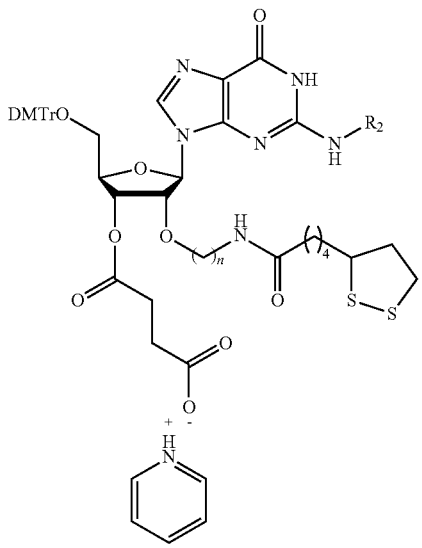

Where
R₁ = H, OH, F, Oalkyl
R₂ = Bz, Ac, DMF, DMA
n = 1-20 carbon atoms

One embodiment of the invention is directed to a nucleoside, comprising: a nucleobase; a ribose; a dithiolane derivative at 2'-O of the ribose; and a solid support at 3'O— of the ribose, wherein the nucleobase is a pyrimidine as represented by Structure 27 or Structure 28, and a purine as represented by Structure 29 or Structure 30:

Structure 27

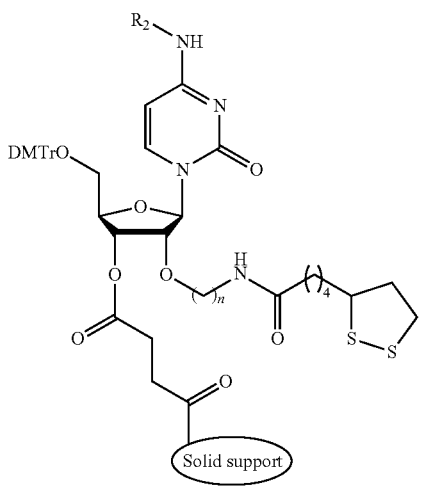

Structure 28

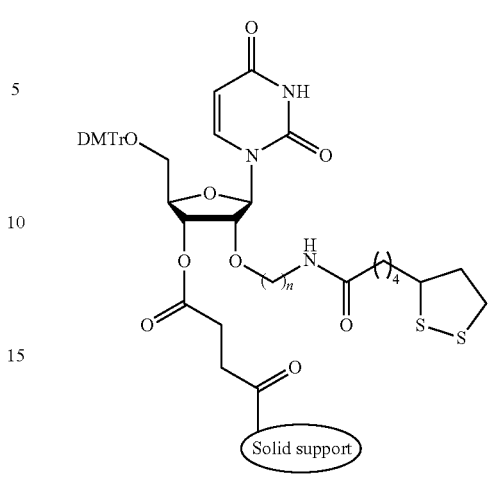

Structure 29

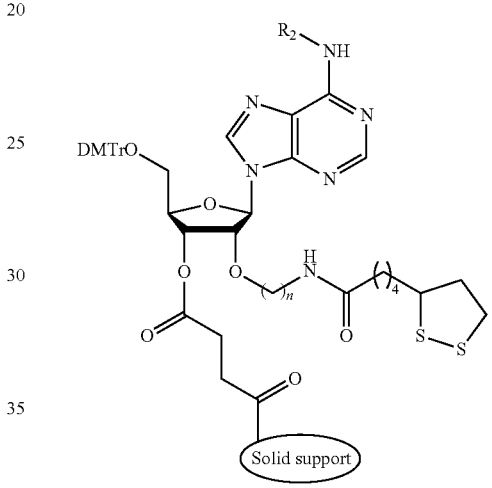

Structure 30

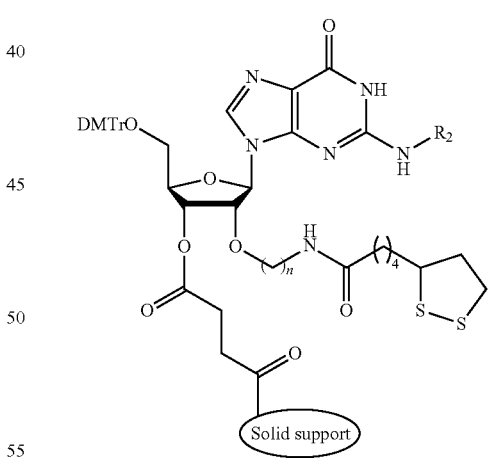

Where
R₁ = H, OH, F, Oalkyl
R₂ = Bz, Ac, DMF, DMA
n = 1-20 carbon atoms

One embodiment of the invention is directed to a nucleoside, comprising a dithiolane derivative according to one of the above-mentioned nucleosides, wherein the nucleoside is represented by one of Structure 1 through Structure 30.

Figure 14:
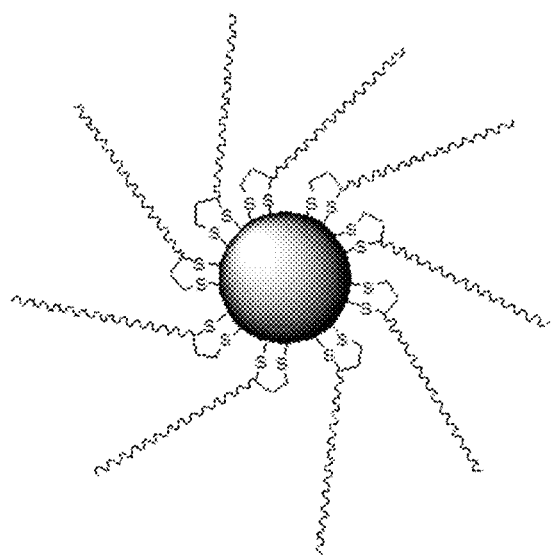
FIG. 14: An illustration of a conjugate of the oligoribonucleotide or the oligodeoxyribonucleotide from as described above with solid supports such as gold, quantum dots.

One embodiment of the invention is directed to a conjugate, comprising: the nucleoside mentioned above, and a solid support, wherein the solid support is gold or quantum, and the conjugate is presented in FIG. 14.

To show this, we have successfully synthesized N2-functionalized deoxy-guanosine amidites (1, Chart 1) and proposed the scheme for the corresponding compound with solid support (2, Chart 1). In addition to these we proposed various dithiolane functionalized DNA and RNA amidites and solid supports (Schemes 1 to 8). These monomers are useful in generating the thiol functionalities at 3'- or 5'-end of oligonucleotides. With these improvements, we strongly believe that our probes are designed to be ideally suited to application in high quality probes consisting of dithiolane moieties.

The thiol modified oligonucleotides have vast number of applications in the field of nucleic acid chemistry such as it enables covalent attachment of a variety of ligands and also has an ability to form relatively stronger bond with gold surface. DNA functionalized gold nanoparticles have become widely used building blocks in key nucleic acid based assembly strategies and therapeutics. Even though thiol group forms relatively stronger bond with elemental gold (about 30-40 K cal/mole), it gets displaced at higher temperature, in high salt concentration buffers and in presence other thiols. For many of applications with these conjugates strong binding of the oligonucleotides to the gold nano particles is required. However to circumvent displacement of thiol, a few cyclic disulfide modifiers that can introduce multiple thiol groups have been introduced in the 15 prior art. Their stability studies revealed that these multi-thiol functionalized oligonucleotides form relatively more stable SAMs compared to the corresponding mono-thiol derivatives. In the present application, we describe the design and efficient synthesis of N2 cyclic dithiolane functionalized phosphoramidite derivative 1 (Chart 1) and proposed synthesis of corresponding dithiolane succinyl CPG supports 2 (Chart 1). In addition to the synthesized dithiolane functionalized derivatives 1 (Chart 1), we envision various other functionalized derivatives compounds from Schemes 1 to 8. Conjugation of dithiolane moiety to the either nucleobase or to sugar part with linker arm should generate very interesting functionalized thiol oligonucleotides. The advantage of relatively long linker arm is that it allows clean formation of the monomers on the solid surfaces and keeps the self-assembled monomers in the optimum distance from the solid support. Pairs of oligonucleotide-gold nano-particle conjugates serve as unique probes for recognizing specific sequences in DNA segments, as building blocks for assembling novel structures, bio diagnostics and nano technology based therapeutics.

2-Fluoro of the nucleoside 53 [Cao, H., Yong, J., Yinsheng W. *Jour. of the Am. Chem. Soc.* 2007, 129, 12123-12130] was displaced by the 1,12-diaminododecane to afford amino nucleoside 54 in 79% yield. Nucleoside 54 was coupled to thioctic acid using EDC.HCl to get N2-dithiolane coupled product 55. Finally, compound 55 was converted to target amidite 1 using N,N'-(diisopropyl)phosphoramidochloriditie reagent and N,N'-diisopropylethylamine in anhydrous THF in 67% yield (Scheme 9). Compound 55 can also be converted to corresponding succinate 57 (Scheme 10) followed by coupling to the suitable solid support to get compound 2 (Scheme 10). These target compounds 1 and 2 can be incorporated into the oligonucleotide sequence to get the dithiolane modification at the either 3'- or 5'-end of the oligonucleotide sequence as depicted in Schemes 9 and 10.

Scheme 1: Synthetic scheme for C5-dithiolane functionalized Uridine amidites and supports.

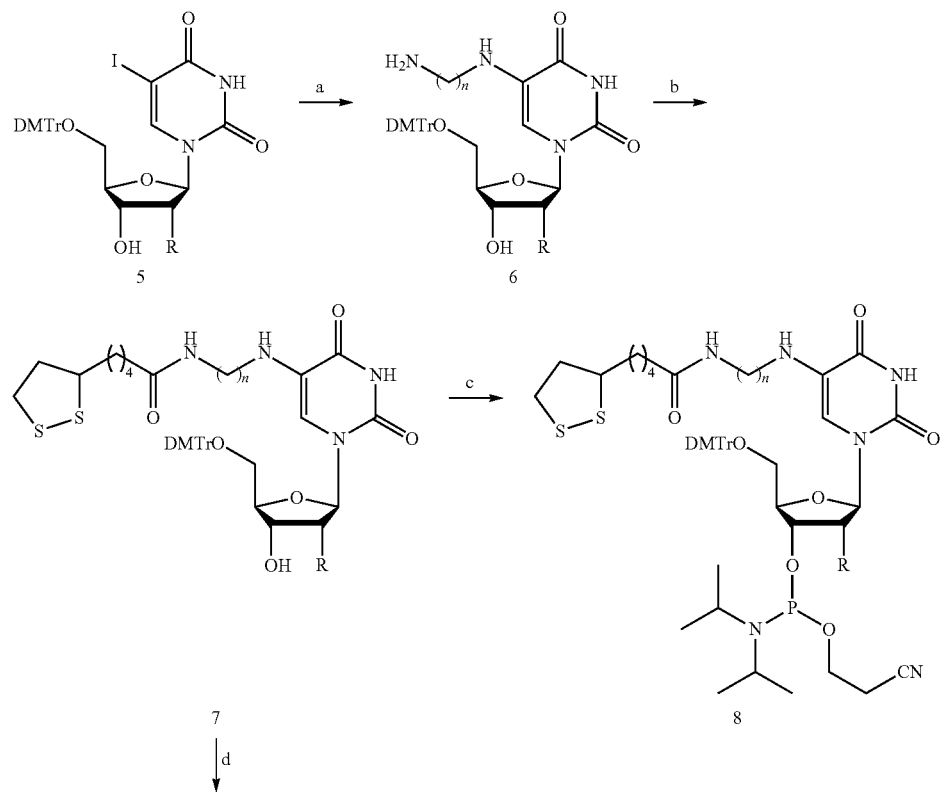

-continued

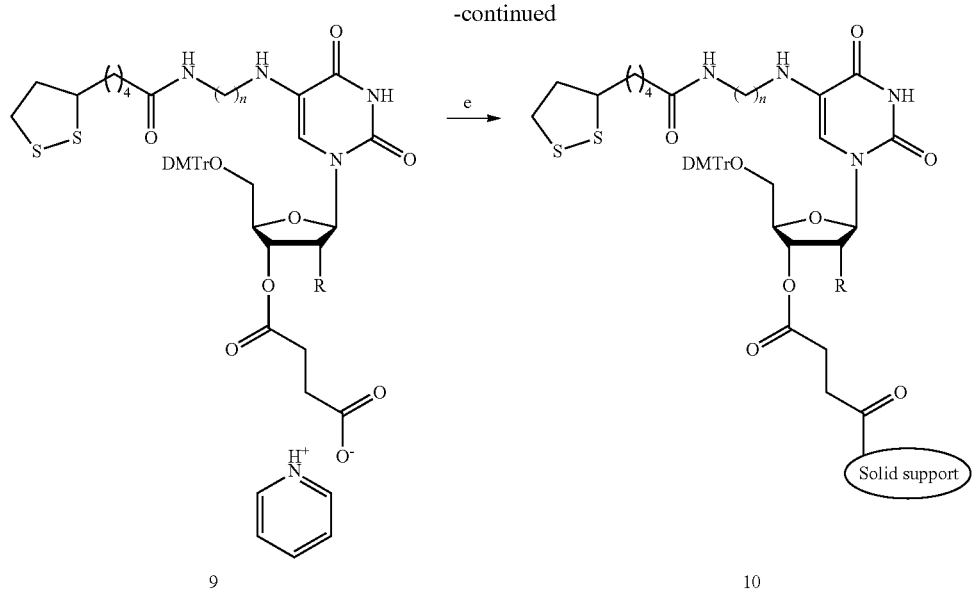

9 → 10

Where
R = H, OH, F, Oalkyl, OCH$_3$
n = 1-20
b) Thioctic acid

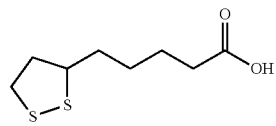

Reagents and Conditions: (a) Corresponding diamine, MeOH; (b) Thioctic acid, EDC•HCl, N,N'-dimethylformamide, rt;
(c) 2-Cyanoethyl N,N'-(diisopropyl)phosphoramidochloridite, N,N'-diisopropylethylamine, anhydrous THF;
(d) Succinic-anhydride, 4-dimethylaminopyridine, anhydrous pyridine; (e) HBTU, N,N'-diisopropylethylamine,
Solid support with amine functionality.

The proposed Scheme 1 outlines synthesis of uridine C-5 spacer moiety, at the terminal of which dithiolane function is attached. Other modification of solid chain at C-5 can be envisioned such as introduction of alkyl carboxy function for further elongation of C-5 and eventually attaching dithiolane function. Besides 2'-deoxy nucleosides 2'-modified nucleosides are also envisioned, such as 2'-F, 2'-Omethyl, 2'-O alkyl, 2'-O-amino (protected). Various chromophores can be attached to this nucleoside as well as the oligonucleotide chain for better and diverse detection applications. Phosphoramidites and succinates are envisioned. The later function can be utilized to attach the compound (9) to various solid support.

Scheme 2: Synthetic scheme for C5-dithiolane functionalized Cytidine amidite and supports

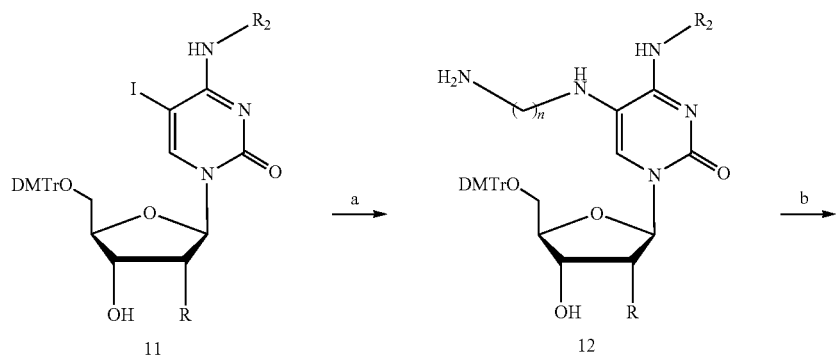

-continued

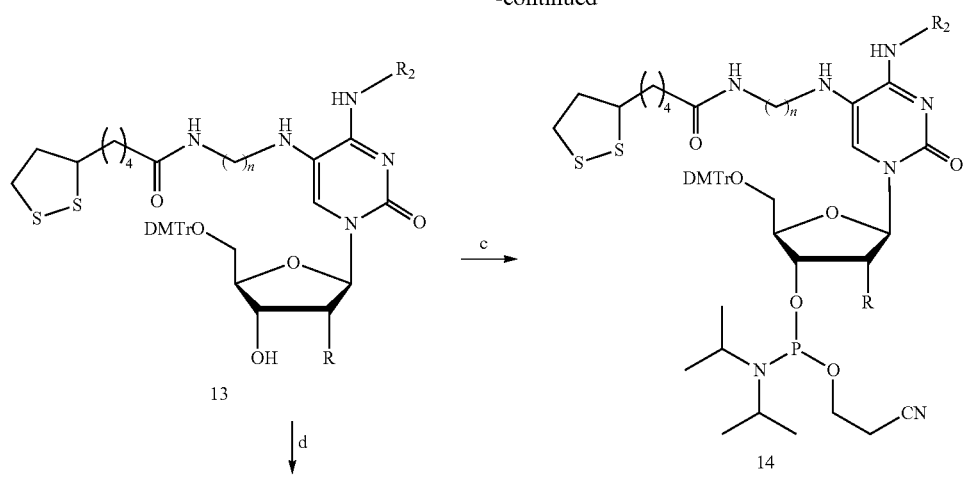

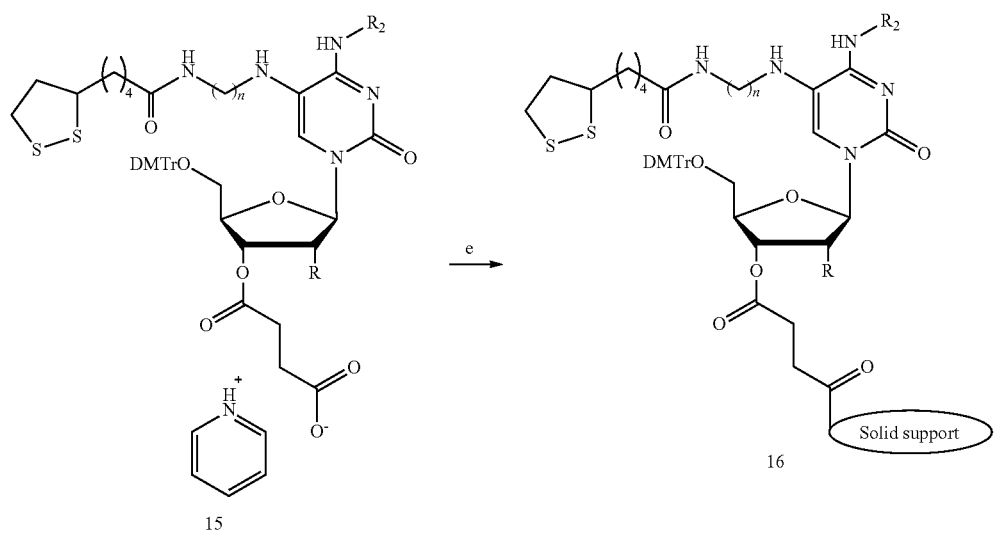

Where
R₁ = H, OH, F, Oalkyl, OCH₃
R₂ = Ac, Bz, DMF (dimethylformamidine)
n = 1-20
b) Thioctic acid

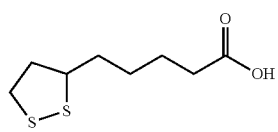

Reagents and Conditions:
a) Corresponding diamine, MeOH;
b) Thioctic acid, EDC•HCl, N,N'-dimethylformamide, rt;
c) 2-Cyanoethyl N,N'-(diisopropyl)phosphoramidochloridite, N,N'-diisopropylethylamine, anhydrous THF;
d) Succinic-anhydride, 4-dimethylaminopyridine, anhydrous pyridine;
e) HBTU, N,N'-diisopropylethylamine, Solid support with amine functionality.

The proposed Scheme 2 outlines synthesis of cytidine C-5 spacer moiety, at the terminal of which dithiolane function is attached. Other modification of solid chain at C-5 can be envisioned such as introduction of alkyl carboxy function for further elongation of C-5 and eventually attaching dithiolane function. Besides 2'-deoxy nucleosides 2'-modified nucleosides are also envisioned, such as 2'-F, 2'-Omethyl, 2'-O alkyl, 2'-O-amino (protected). Various chromophores can be attached to this nucleoside as well as to oligonucleotide chain for better and diverse detection applications. Phosphoramidites and succinates are envisioned. The later function can be utilized to attach the compound (15) to various solid support

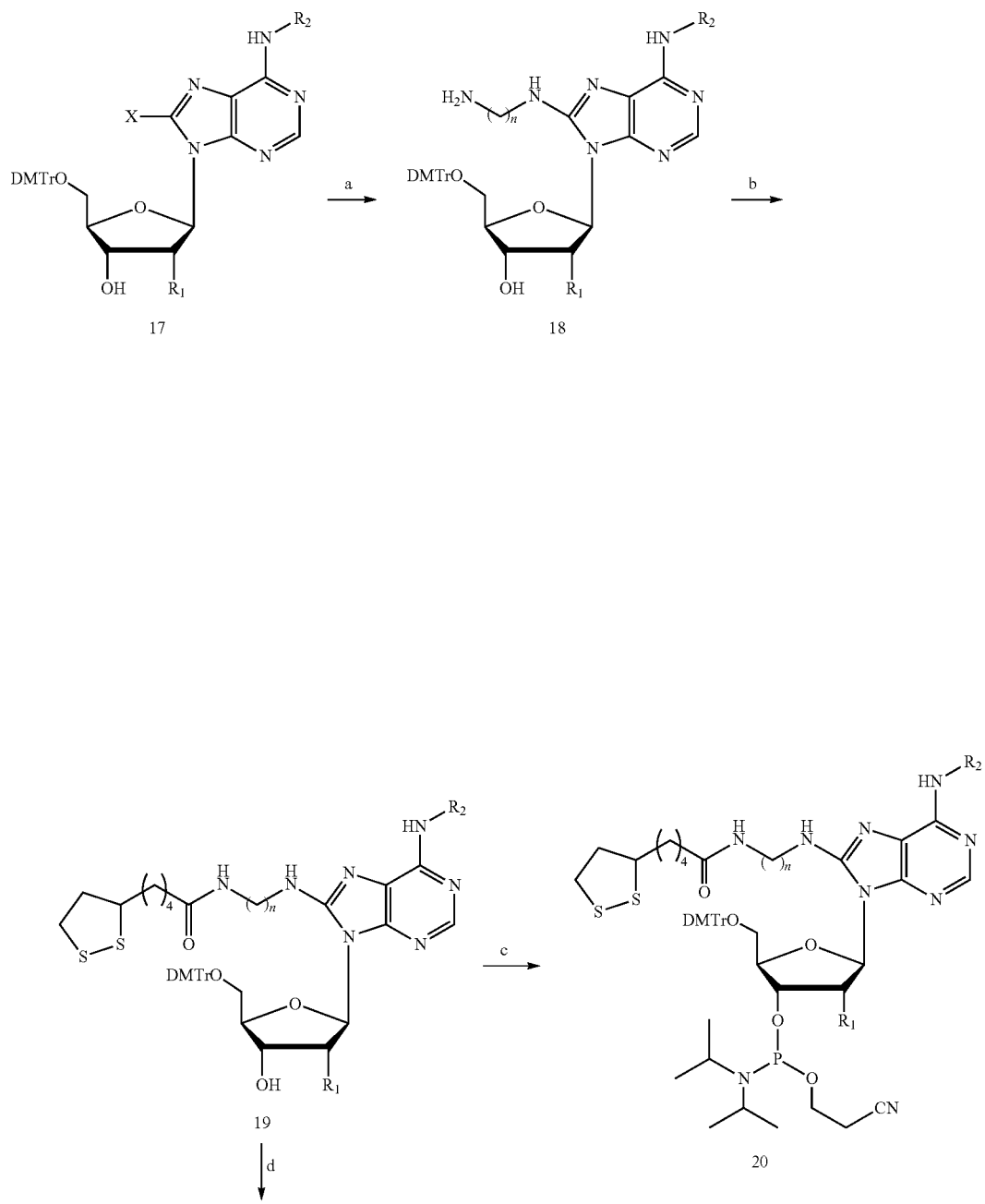

Scheme 3: Synthetic scheme for C8-dithiolane functionalized Adenosine amidite and supports

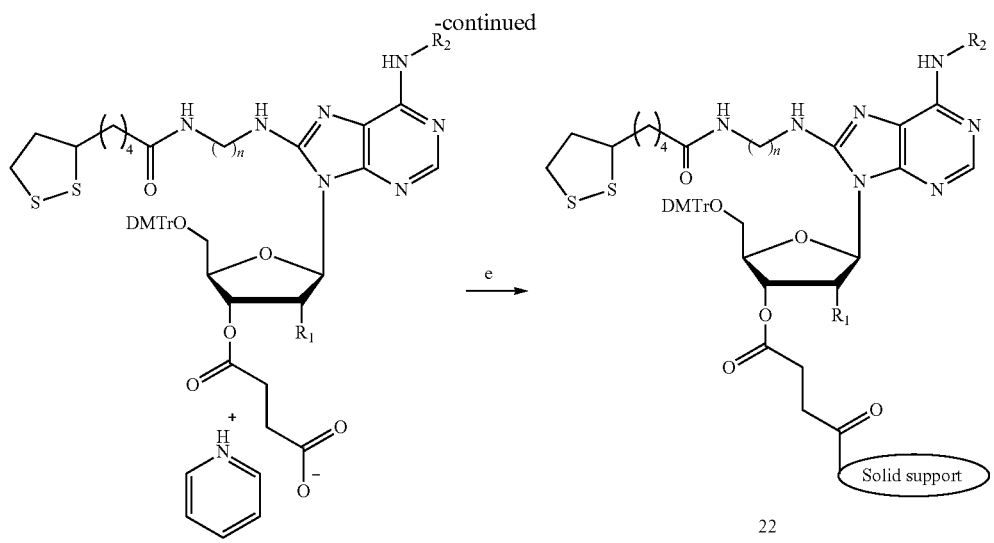

Where
R₁ = H, OH, F, Oalkyl, OCH₃
R₂ = Bz, Ac and DMA
n = 1-20
X = Br, Iodo b) Thioctic acid

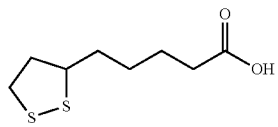

Reagents and Conditions:
a) Corresponding diamine, MeOH;
b) Thioctic acid, EDC•HCl, N,N'-dimethylformamide, rt;
c) 2-Cyanoethyl N,N'-(diisopropyl)phosphoramidochloridite, N,N'-diisopropylethylamine, anhydrous THF;
d) Succinic-anhydride, 4-dimethylaminopyridine, anhydrous pyridine;
e) HBTU, N,N'-diisopropylethylamine, Solid support with amine functionality.

The proposed Scheme 3 outlines synthesis of deoxy adenosine C-8 spacer moiety, at the terminal of which dithiolane function is attached. Other modification of solid chain at C-8 can be envisioned such as introduction of C-8-O-alkyl function for further elongation of C-8 and eventually attaching dithiolane function. Besides 2'-deoxy nucleosides 2'-modified nucleosides are also envisioned, such as 2'-F, 2'-Omethyl, 2'-O alkyl, 2'-O-amino (protected). Various chromophores can be attached to this nucleoside as well as to oligonucleotide chain for better and diverse detection applications. Phosphoramidites and succinates are envisioned. The later function can be utilized to attach the compound (21) to various solid support.

Scheme 4: Synthetic scheme for C8-dithiolane functionalized Guanosine amidite and supports.

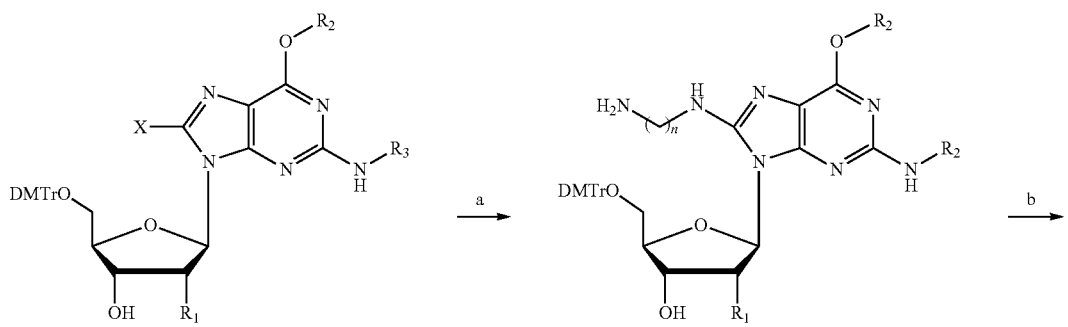

-continued

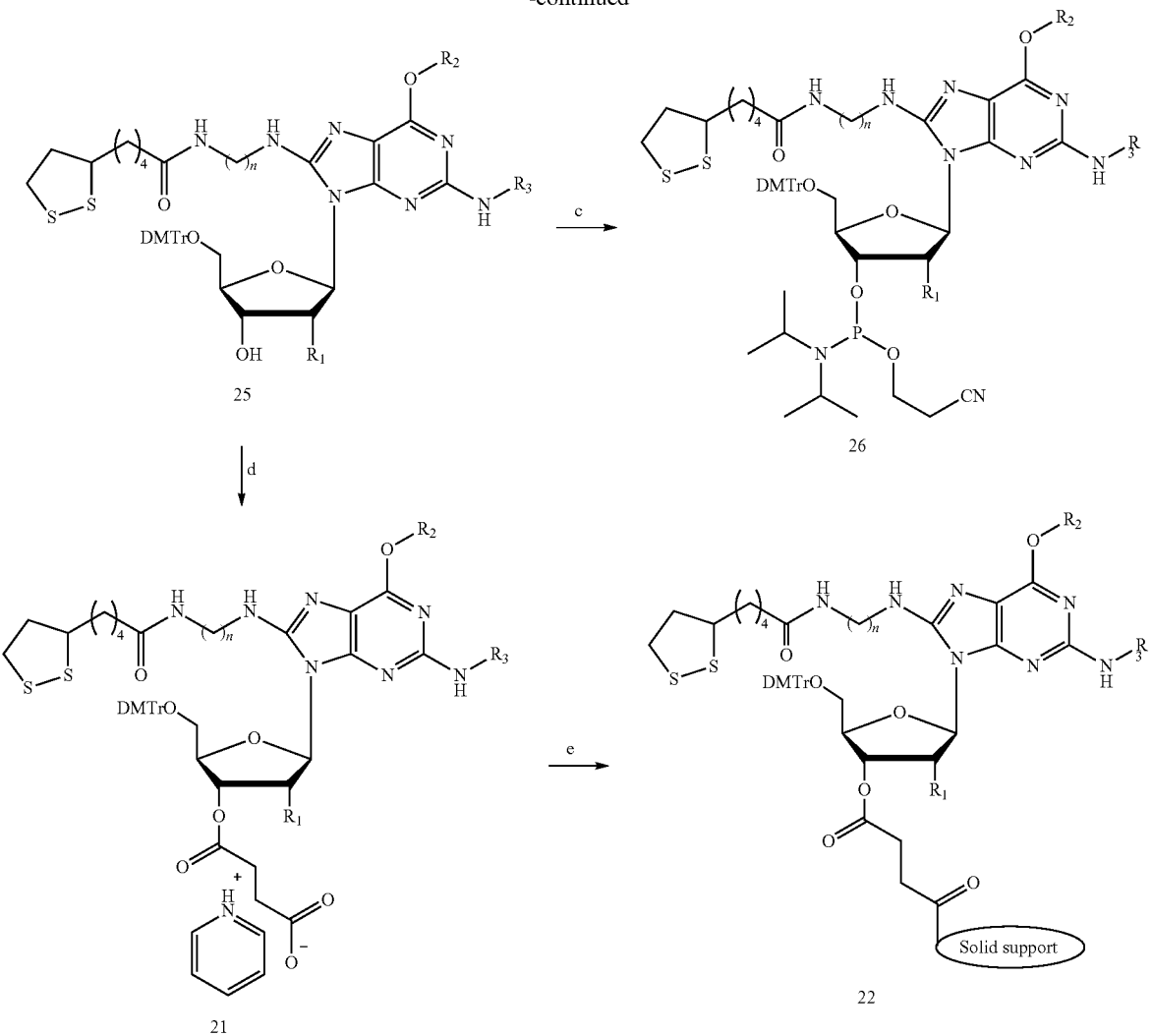

25

26

21

22

Where
R₁ = H, OH, F, Oalkyl, OCH₃
R₂ = Ethytrimethylsilyl, Cyanoethyl
R₃ = Bz, Ac and DMA
n = 1-20
X = Br, Iodo b) Thioctic acid

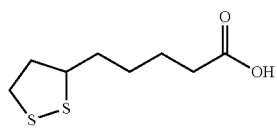

Reagents and Conditions:
a) Corresponding diamine, MeOH;
b) Thioctic acid, EDC•HCl, N,N'-dimethylformamide, rt;
c) 2-Cyanoethyl N,N'-(diisopropyl)phosphoramidochloridite, N,N'-diisopropylethylamine, anhydrous THF;
d) Succinic-anhydride, 4-dimethylaminopyridine, anhydrous pyridine;
e) HBTU, N,N'-diisopropylethylamine, Solid support with amine functionality.

The proposed Scheme 4 outlines synthesis of guanosine C-8 spacer moiety, at the terminal of which dithiolane function is attached. Other modification of solid chain at C-8 can be envisioned such as introduction of 8-O-alkyl function for further elongation of C-8 and eventually attaching dithiolane function. Besides 2'-deoxy nucleosides, 2'-modified nucleosides are also envisioned, such as 2'-F, 2'-Omethyl, 2'-O alkyl, 2'-O-amino (protected). Various chromophores can be attached to this nucleoside as well as to oligonucleotide chain for better and diverse detection applications. Phosphoramidites and succinates are envisioned. The later function can be utilized to attach the compound (27) to various solid support. In the proposed Scheme 4, O6 has been protected with a protecting group, which can be removed under mild conditions to generate free O6 carbonyl function of guanosine.

Scheme 5: Synthetic scheme for 2'-O-dithiolane functionalized Uridine amidite and supports.

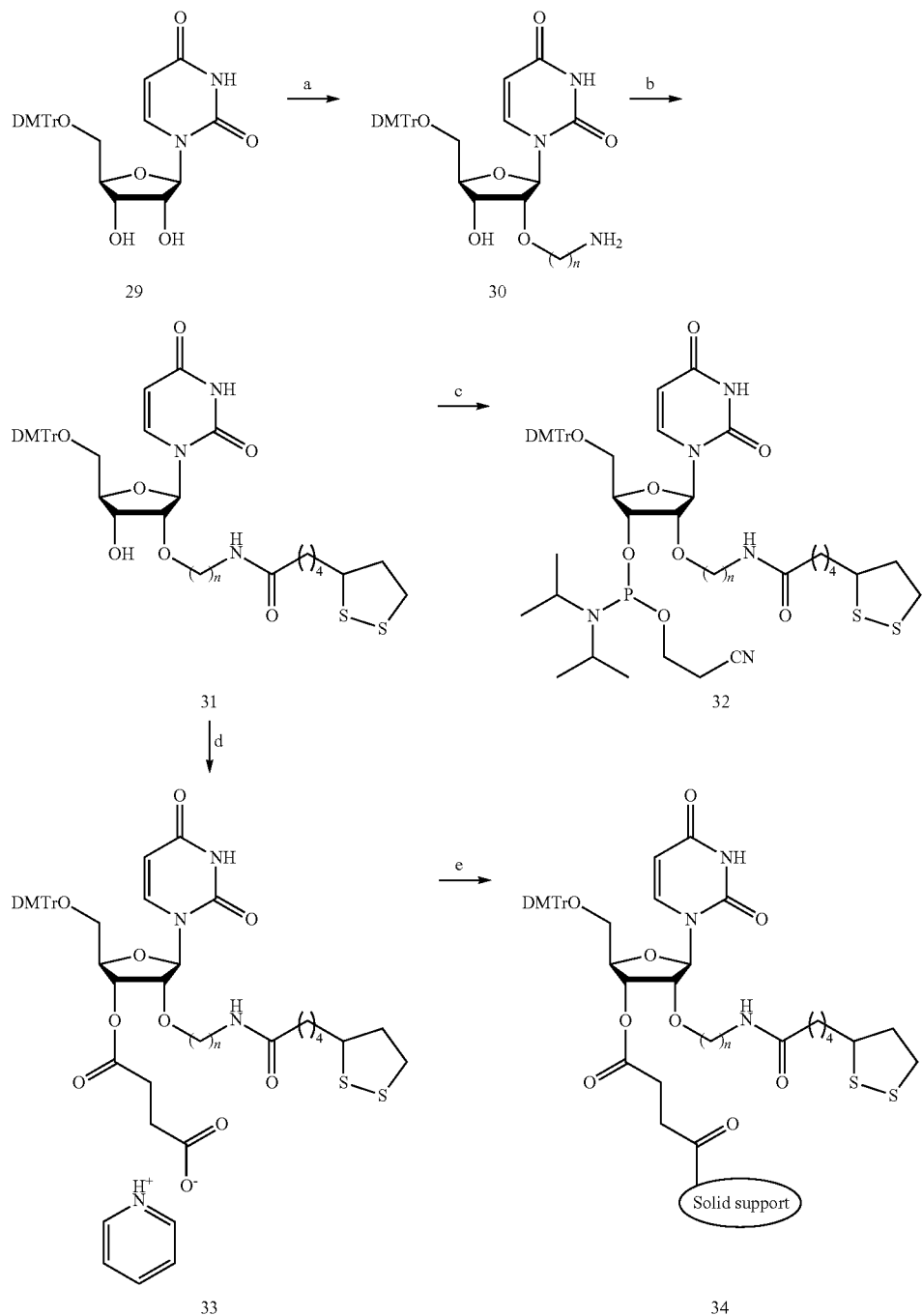

Where
n = 1-20
b) Thioctic acid

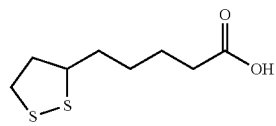

Reagents and Conditions: a); b) Thioctic acid, EDC·HCl, N,N'-dimethylformamide, rt;
c) 2-Cyanoethyl N,N'-(diisopropyl)phosphoramidochloridite, N,N'-diisopropylethylamine, anhydrous THF;
d) Succinic-anhydride, 4-dimethylaminopyridine, anhydrous pyridine; e) HBTU, N,N'-diisopropylethylamine,
Solid support with amine functionality.

The proposed Scheme 5 outlines synthesis of uridine 2'-O-alkyl spacer moiety, at the terminal of which dithiolane function is attached. Other modification of solid chain at 2'-O— can be envisioned such as introduction of alkyl carboxy function for further elongation of O-2'- and eventually attaching dithiolane function. Various chromophores can be attached to this nucleoside to synthesize oligonucleotide chains for better and diverse detection applications. Phosphoramidites and succinates are envisioned. The later function can be utilized to attach the compound (33) to various solid support.

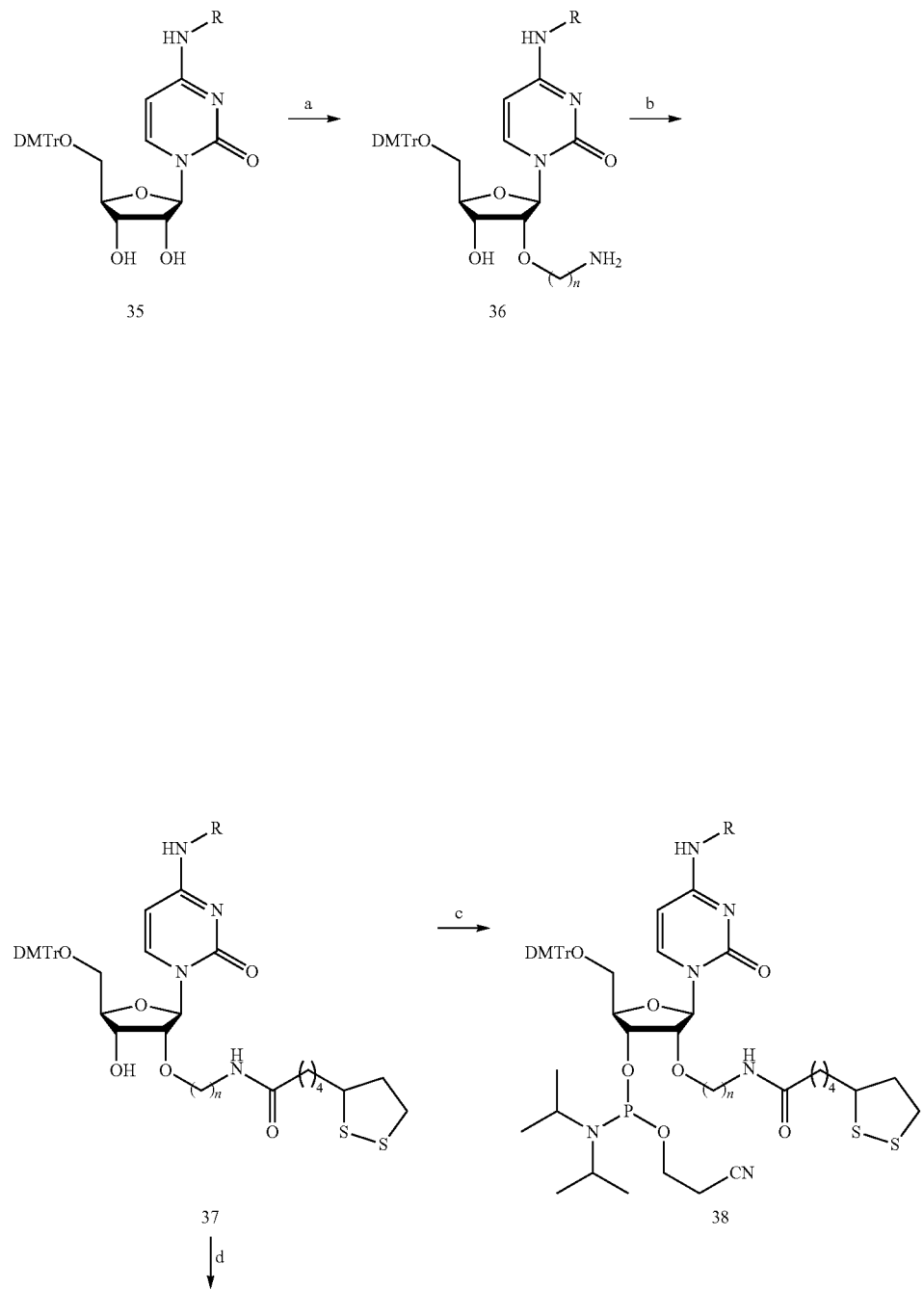

Scheme 6: Synthetic scheme for 2'-O-dithiolane functionalized Cytidine amidite and supports.

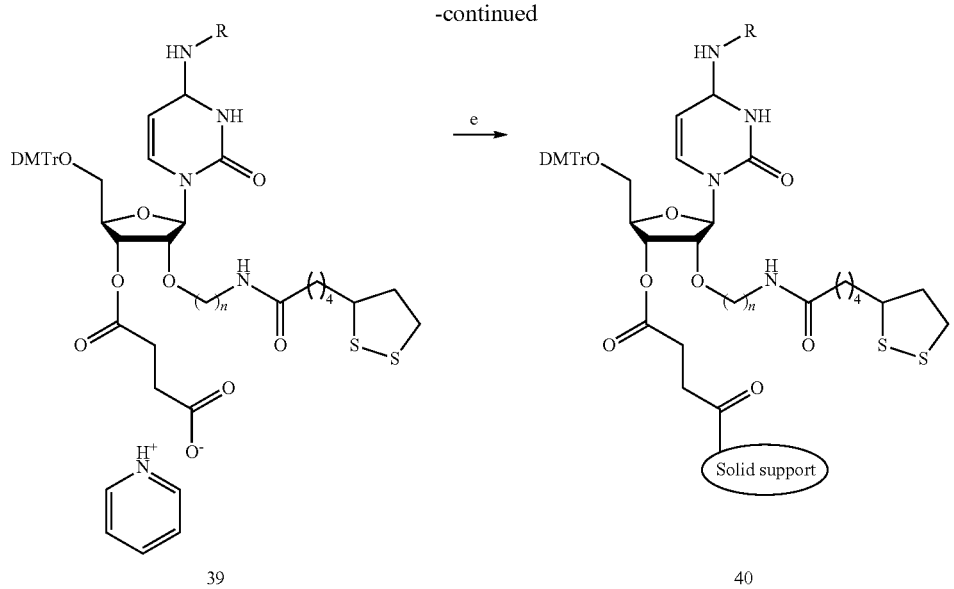

39    40

Where
R = Ac, Bz, DMF (dimethyl formamidine)
n = 1-20
b) Thioctic acid

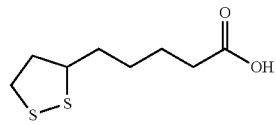

Reagents and Conditions: a); b) Thioctic acid, EDC•HCl, N,N'-dimethylformamide, rt;
c) 2-Cyanoethyl N,N'-(diisopropyl)phosphoramidochloridite, N,N'-diisopropylethylamine, anhydrous THF;
d) Succinic-anhydride, 4-dimethylaminopyridine, anhydrous pyridine; e) HBTU, N,N'-diisopropylethylamine, Solid support with amine functionality.

The proposed Scheme 6 outlines synthesis of cytidine 2'-O-alkyl spacer moiety, at the terminal of which dithiolane function is attached. Other modification of side chain at 2'-O— can be envisioned such as introduction of 2'-O-alkyl carboxy function for further elongation of O-2'- and eventually attaching dithiolane function. Various chromophores can be attached to this nucleoside to synthesize oligonucleotide chains for better and diverse detection applications. Phosphoramidites and succinates are envisioned. The later function can be utilized to attach the compound (39) to various solid support.

Scheme 7: Synthetic scheme for 2'-O-dithiolane functionalized Adenosine amidite and supports.

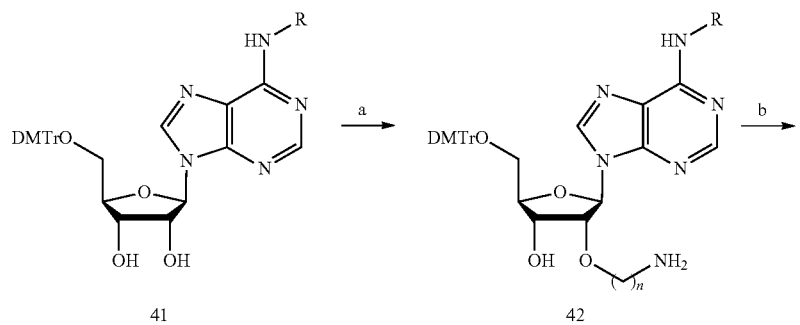

41    42

-continued

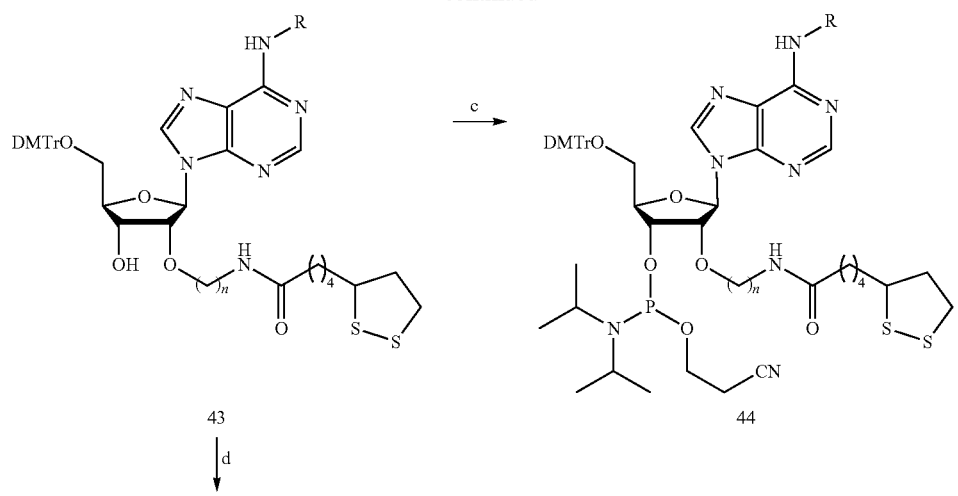

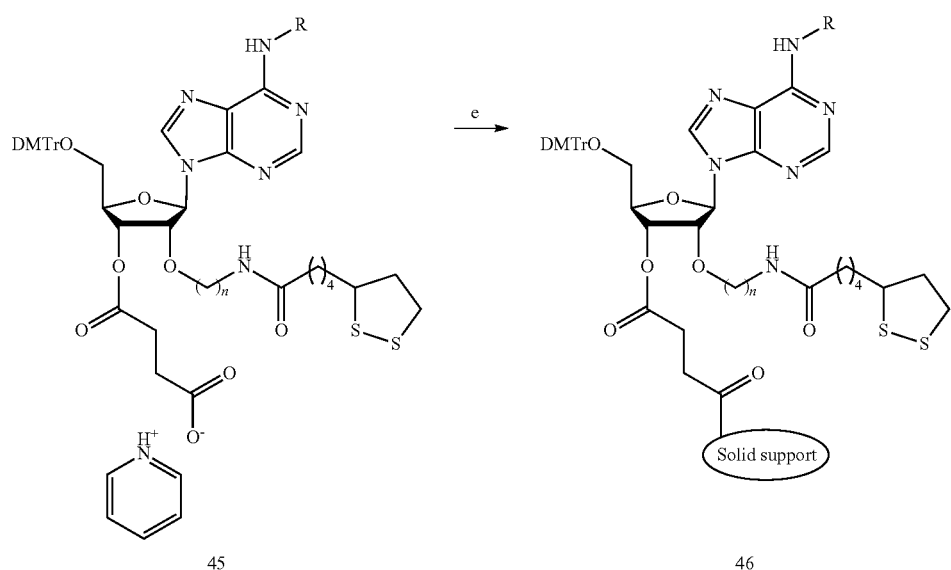

Where
R = Bz, Ac and DMA
n = 1-20
b) Thioctic acid

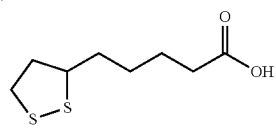

Reagents and Conditions: a); b) Thioctic acid, EDC•HCl, N,N'-dimethylformamide, rt;
c) 2-Cyanoethyl N,N'-(diisopropyl)phosphoramidochloridite, N,N'-diisopropylethylamine, anhydrous THF;
d) Succinic-anhydride, 4-dimethylaminopyridine, anhydrous pyridine; e) HBTU, N,N'-diisopropylethylamine,
Solid support with amine functionality.

The proposed Scheme 7 outlines synthesis of adenosine 2'-O-alkyl spacer moiety, at the terminal of which dithiolane function is attached. Other modification of side chain at 2'-O— can be envisioned such as introduction of 2'-O-alkyl carboxy function for further elongation of O-2'- and eventually attaching dithiolane function. Various chromophores can be attached to this nucleoside to synthesize oligonucleotide chains for better and diverse detection applications. Phosphoramidites and succinates are envisioned. The later function can be utilized to attach the compound (45) to various solid support.

Scheme 8: Synthetic scheme for 2'-O-dithiolane functionalized Guanosine amidite and supports.

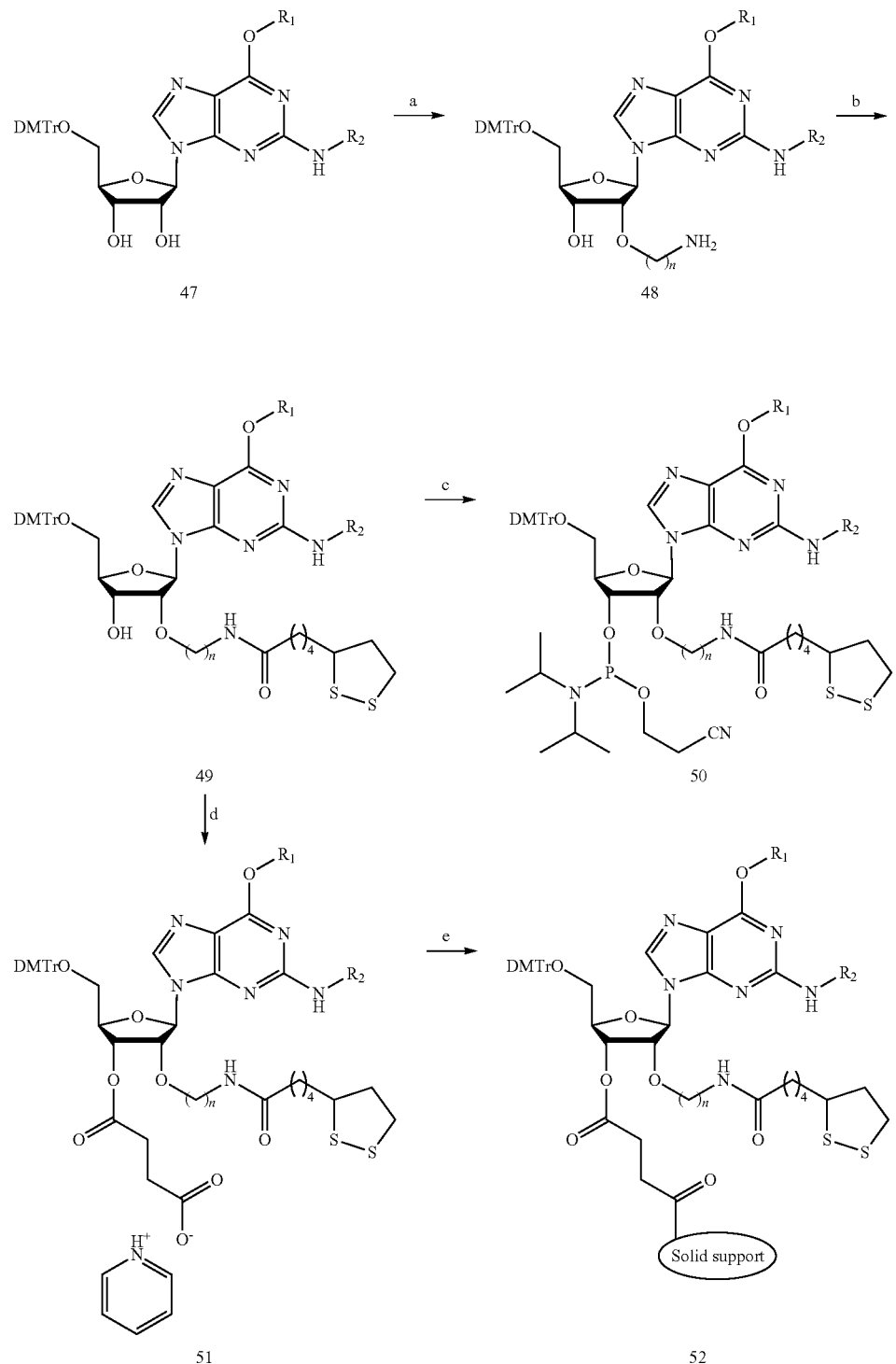

Where
$R_1$ = Ethyltrimethylsilyl, Cyanoethyl
$R_2$ = Bz, Ac and DMA
n = 1-20
b) Thioctic acid

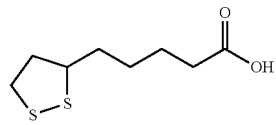

Reagents and Conditions: a); b) Thioctic acid, EDC·HCl, N,N′-dimethylformamide, rt;
c) 2-Cyanoethyl N,N′-(diisopropyl)phosphoramidochloridite, N,N′-diisopropylethylamine, anhydrous THF;
d) Succinic-anhydride, 4-dimethylaminopyridine, anhydrous pyridine; e) HBTU, N,N′-diisopropylethylamine, Solid support with amine functionality.

The proposed Scheme 8 outlines synthesis of guanosine 2′-O-alkyl spacer moiety, at the terminal of which dithiolane function is attached. Other modification of side chain at 2′-O— can be envisioned such as introduction of 2′-O-alkyl carboxy function for further elongation of O-2′- and eventually attaching dithiolane function. Various chromophores can be attached to this nucleoside to synthesize oligonucleotide chains for better and diverse detection applications. Phosphoramidites and succinates are envisioned. The later function can be utilized to attach the compound (51) to various solid support.

In the proposed Scheme 8, O6 has been protected with a protecting group, which can be removed under mild conditions to generate free O6 carbonyl function of guanosine.

Scheme 9: Synthesis of N2-guanosine functionalized dithiolane phosphoramidite and the corresponding oligonucleotides.

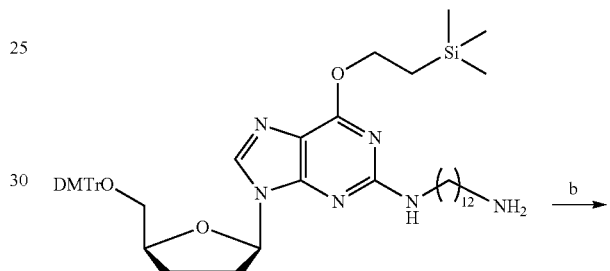

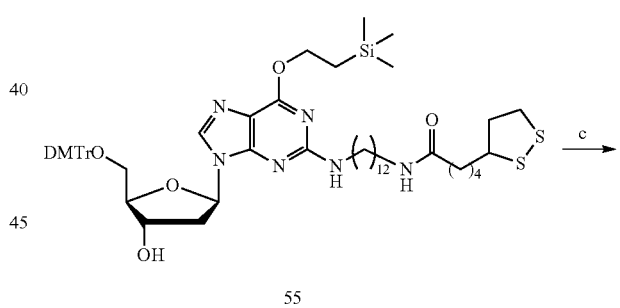

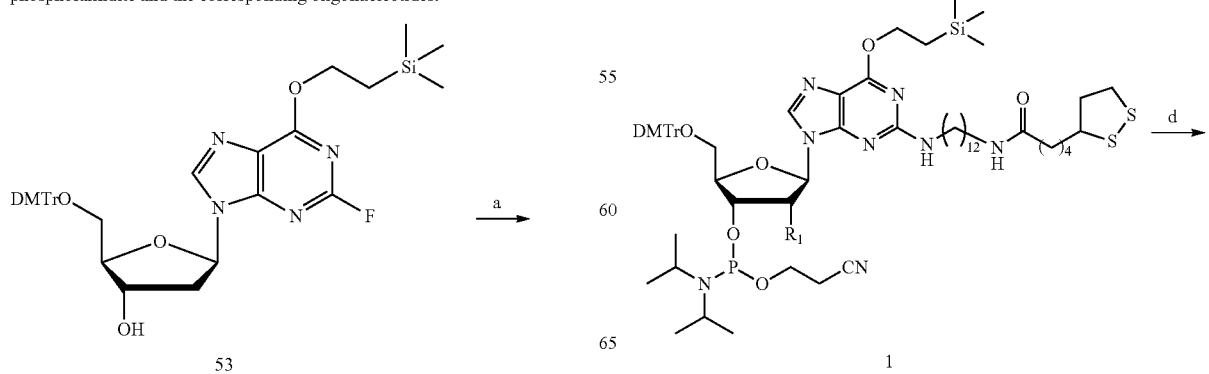

53

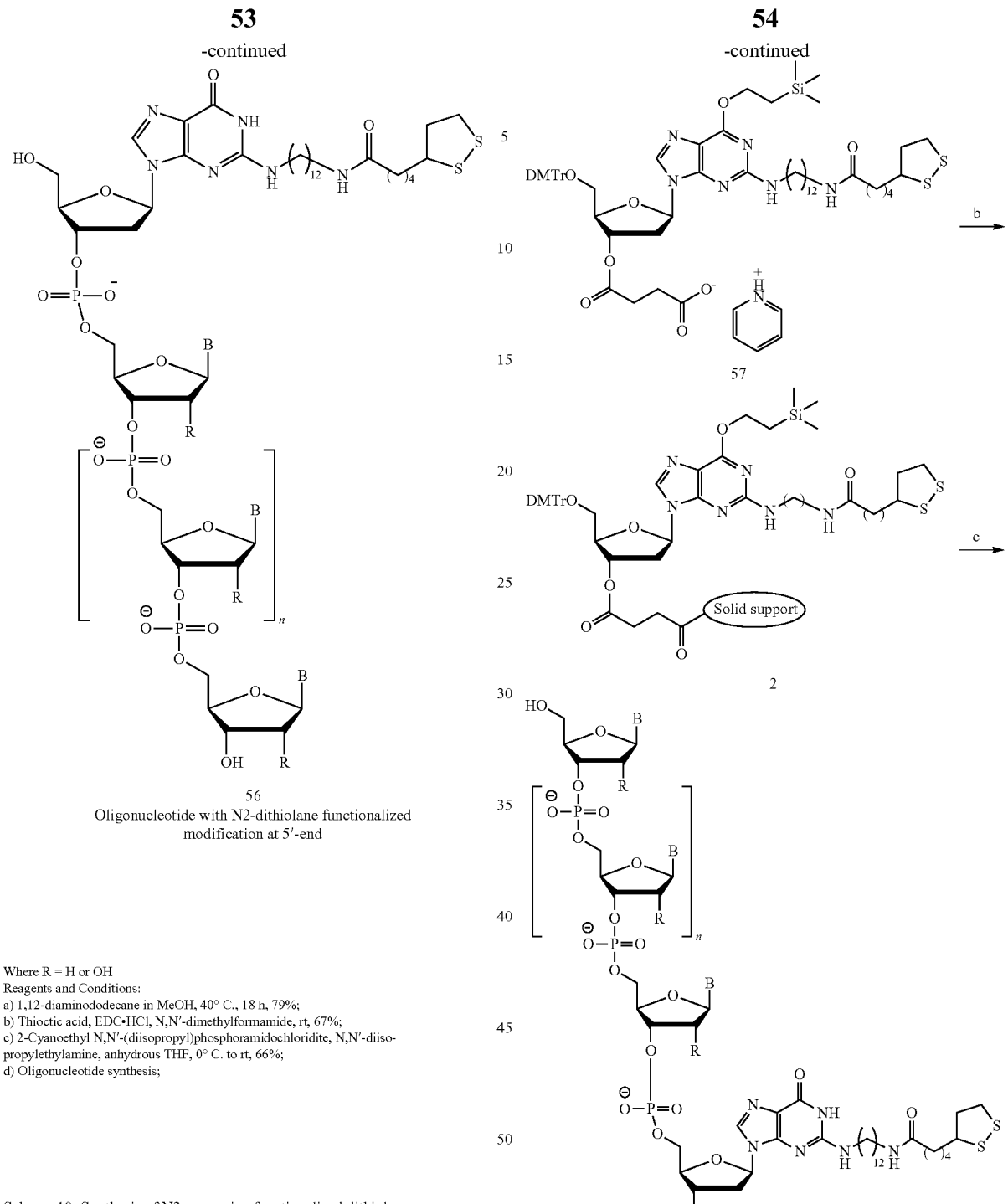

56
Oligonucleotide with N2-dithiolane functionalized modification at 5′-end

Where R = H or OH
Reagents and Conditions:
a) 1,12-diaminododecane in MeOH, 40° C., 18 h, 79%;
b) Thioctic acid, EDC•HCl, N,N′-dimethylformamide, rt, 67%;
c) 2-Cyanoethyl N,N′-(diisopropyl)phosphoramidochloridite, N,N′-diisopropylethylamine, anhydrous THF, 0° C. to rt, 66%;
d) Oligonucleotide synthesis;

Scheme 10: Synthesis of N2-guanosine functionalized dithiolane solid supports and subsequent synthesis of oligonucleotides.

54

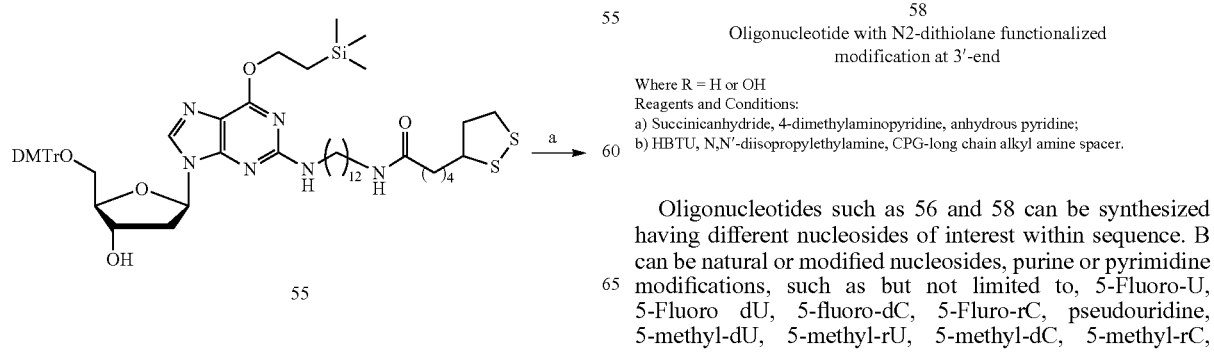

58
Oligonucleotide with N2-dithiolane functionalized modification at 3′-end

Where R = H or OH
Reagents and Conditions:
a) Succinicanhydride, 4-dimethylaminopyridine, anhydrous pyridine;
b) HBTU, N,N′-diisopropylethylamine, CPG-long chain alkyl amine spacer.

Oligonucleotides such as 56 and 58 can be synthesized having different nucleosides of interest within sequence. B can be natural or modified nucleosides, purine or pyrimidine modifications, such as but not limited to, 5-Fluoro-U, 5-Fluoro dU, 5-fluoro-dC, 5-Fluro-rC, pseudouridine, 5-methyl-dU, 5-methyl-rU, 5-methyl-dC, 5-methyl-rC, 5-bromo-dU, 5-bromo-rU, 5-bromo-dC, 5-bromo-rC, 5-iodo-dU, 5-iodo-rU, 5-vinyl-dU, 5-vinyl-rU, 5-vinyl thymidine, N-3 methyldeoxy uridine, N-3 methyl-ribouridine, N-3 methyl thymidine, 4-thio uridine, 4-thio-2'-deoxyuridine, 2,6-diaminopurine deoxy riboside, N-3 methyl ribothymidine, 2,6-diaminopurine riboside, 8-bromo 2'-deoxy adenosine, 8-bromo-r-adenosine, 8-oxo-deoxy adenosine, 8-oxo-riboadenosine, 8-oxo-2'-deoxy-adenosine, 8-oxo-riboadenosine, 8-oxo-deoxy inosine, 8-oxo-ribo inosine, 8-bromo-deoxy inosine, 8-bromo-ribo-inosine, N-1 methyl-riboadenosine, N-1 methyl-2'-deoxy adenosine, N-1 methyl 2'-deoxy inosine, N-1 methyl riboadenosine, N-1 methyldeoxy guanosine, N-1-methyl-riboguanosine, etheno adenosine, etheno 2'-deoxy adenosine, purine 2'-deoxy riboside, purine-ribonucleoside, 2-aminopurine-2'-deoxyriboside, 2-aminopurine-ribonucleoside. Labelling of internal positions of a DNA synthesized by this method is achievable with chromophores such as, but not limited to Fluoroscein-C-5 dT, Dabcyl-C-5 thymidine, internal carboxyl group 5-dU-methylacrylate, biotin dT (biotin attached via spacer to C-5 of dU), amino-dT (terminal amino attached via C-6 spacer to C-5 dU). The sugar modification of modified nucleosides could consist of 2'-deoxy-2'-fluoro ribo nucleosides (2'-F-ANAs) such as A, C, G, U, Inosine and modified nucleosides containing 2'-Fluoro, in one or more positions of an RNA or DNA sequence synthesized by the method of this invention.

The sugar modification of modified nucleosides could consist of 2'-deoxy-2'-methoxy ribo nucleosides (2'-OMe-) such as A, C, G, U, Inosine and modified nucleosides containing 2'-methoxy, in one or more positions of an RNA or DNA sequence synthesized by this method. The sugar modification of modified nucleosides could consist of 2'-deoxy-2'-amino ribo nucleosides (2'-NH2) such as A, C, G, U, Inosine and modified nucleosides containing 2'-amino, in one or more positions of an RNA or DNA sequence synthesized by this method. The sugar modification of modified nucleosides could consist of 2'-deoxy-2'-terminal amino ribo nucleosides (2'-terminal NH2), attached via spacer from 2-10 atoms on nucleosides such as A, C, G, U, Inosine and modified nucleosides containing 2'-terminal amino, in one or more positions of an RNA or DNA sequence synthesized by this method. The sugar modification of modified nucleosides could consist of 2'-deoxy-2'-methoxy ethoxy ribo nucleosides (2'-MOE), such as A, C, G, U, Inosine and modified nucleosides containing 2'-MOE, in one or more positions of an RNA or DNA sequence synthesized by this method. The sugar modification of modified nucleosides could consist of other 2'-O-alkyl groups, such as 2'-deoxy-2'-ethoxy, propargyl, butyne ribo nucleosides (2'-OEt, O-Propargyl, 2'-O-Butyne), such as A, C, G, U, Inosine and modified nucleosides containing 2'-2'-OEt, O-Propargyl, 2'-O-Butyne, in one or more positions of an RNA or DNA sequence synthesized by this method.

Example 1

2-(12-Aminododecanyl)-2'-deoxy-5'-O-(4,4'-Dimethoxytrityl)-O6-(2-trimethylsilylethyl)-Guanosine (54)

2-Fluoro-2'-deoxy guanosine nucleoside (5 g, 7.9 mmol) was dissolved in freshly prepared 1,12-diaminododecane in MeOH (79 mmol, 10:90, v/v). After stirring the reaction mixture at 40° C. for 18 hr it was evaporated to dryness and purified by silica gel column chromatography using $CHCl_3$:Triethylamine:MeOH (95:5:0 to 91:5:4, v/v/v) to afford the compound 54 (5 gr, 79%) as white solid material $R_f$=0.5 (Chloroform:methanol:TEA; 90:05:05) MS m/z ([M+H]$^+$ 854.2, calcd 853.18), MS m/z ($C_{48}H_{68}N_6O_6Si$) [M−H]$^-$ 852.4, calcd 853.18); $^1$H NMR (DMSO, d$^6$) 7.91 (s, 1H), 7.32-7031 (d, 2H), 7.22-7.15 (m, 7H), 6.80-6.74 (m, 5H), 6.25-6.22 (t, 1H), 4.51 (s, 2H), 4.42 (s, 1H), 3.94-3.91 (q, 1H), 3.71-3.70 (d, 6H), 3.28-2.83 (m, 13H), 2.42-2.39 (q, 1H), 2.29-2.26 (q, 1H), 1.46 (s, 2H), 1.31-0.91 (m, 23H), HPLC analysis single peak at 11.257 min (65 to 98% acetonitrile in 0.1M TEAA buffer) and purity is 98.54%.

Example 2

2'-Deoxy-5'-O-(4,4'-Dimethoxytrityl)-2-(12-(5-(1,2-dithiolan-3-yl)pentanamide)-dodecyl)-O6-(2-trimethylsilylethyl)-Guanosine (55)

The compound 54 (2.5 g, 2.93 mmol) was dissolved in anhydrous N,N'-dimethylformamide (25 mL) and EDC.HCL (3.1 g, 16.11 mmol) was added to this. After stirring the reaction for 30 min, thioctic acid (3.02 g, 14.65 mmol) was added at room temperature. After stirring the reaction for 16 h at room temperature, it was evaporated to dryness and purified by silica gel column chromatography ($CHCl_3$:Hexane:Acetone:Triethylamine:MeOH, 47:30:20:1:2, v/v/v/v/v) to afford the compound 55 (2.4 g, 67%) as white solid material. $R_f$=0.6 ($CHCl_3$:Hexane:Acetone:Triethylamine:MeOH, 47:30:20:1:2, v/v/v/v/v); MS m/z $C_{56}H_{80}N_6O_7S_2Si$ ([M+H]$^-$ 1042.2, calcd 1041.18) [M−H]$^-$ 1040.3, calcd 1041.18); $^1$H NMR (DMSO-d6/D$_2$O) 8.23 (s, 1H), 7.92 (s, 1H), 7.92 (s, 1H), 7.73-7.75 (t, 1H), 7.28-7.29 (t, 2H), 7.13-7.19 (m, 7H), 6.71-6.77 (dd, 4H), 6.21-6.23 (t, 1H), 4.43-4.49 (q, 3H), 3.92-3.93 (d, 1H), 3.68-3.69 (d, 6H), 3.52-3.56 (q, 8H), 2.96-3.16 (m, 8H), 2.87 (s, 12H), 2.71 (s, 11H), 2.26-2.36 (m, 1H), 2.01-2.06 (m 1H), 2.01-2.04 (t, 2H), 1.80-1.82 (m 1H), 1.46-1.48 (m, 5H), 1.10-1.48 (m 23H). HPLC analysis single peak at 6.527 min (0 to 50% acetonitrile in 0.1M TEAA buffer) and purity is 97.21%

Example 3

3'-(2-Cyanoethyl diisopropylphosphoramidite)-2'-deoxy-5'-O-(4,4'-dimethoxytrityl)-2-(12-(5-(1,2-dithiolan-3-yl)pentanamide)-dodecyl)-O6-(2-trimethylsilylethyl)-Guanosine (1)

DMT-dithiolane coupled nucleoside 55 (2.4 g, 2.3 mmol) was dried by coevaporation with anhydrous $CH_3CN$ (1×25 mL) and dried over-night on high vacuum pump then dissolved in anhydrous THF (25 mL). To this was added N,N'-diisopropylethylamine (1.2 mL, 6.9 mmol) and cooled in an ice cold water bath. After bubbling the argon for 25 min, 2-cyanoethyl N,N'-(diisopropyl)phosphoramidochloridite (0.565 mL, 2.53 mmol) was added under complete argon atmosphere and the reaction mixture was stirred in ice-cold water bath for 1 h, whereupon it was diluted with EtOAc (100 mL). The organic phase was washed with saturated aqueous $NaHCO_3$ (100 mL), and saturated aqueous NaCl (100 ml). The combine aqueous phase was back-extracted with EtOAc (250 mL). The combined organic phase was evaporated to dryness, and the resulting residue was purified by silica gel column chromatography (29:70:01 Hexane:EtOAc:Triethylamine, v/v/v) to afford target amidite 1 (1.5 g, 66%) as an colorless oil. $R_f$=0.5 (EtOAc:Hexane:Triethylamine, 70:29:01, v/v/v). MS m/z $C_{65}H_{97}N_8O_8PS_2Si$ ([M+H]$^+$1242.3, calcd 1241.58). 31P NMR ($CDCl_3$) 149.527 and 149.196 ppm. HPLC analysis double peak at 14.924 and 16.271 min (0-30% acetoinitrile in 0.1M TEAA buffer) and purity is 99.33%.

What is claimed is:
1. A nucleoside, comprising:
   a guanine;
   a 2'-deoxyribose;

a dithiolane derivative at N2 of the guanine; and
a phosphoramidite derivative at 3' or a solid support at 3',
wherein the nucleoside is Structure 1 or Structure 2:

Structure 1

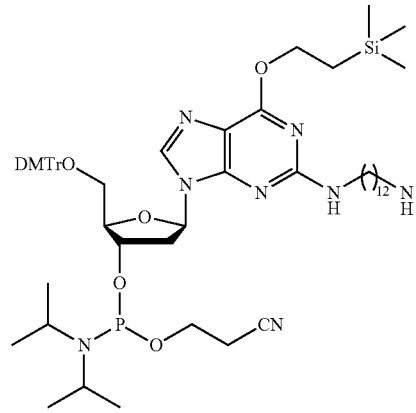

Structure 2

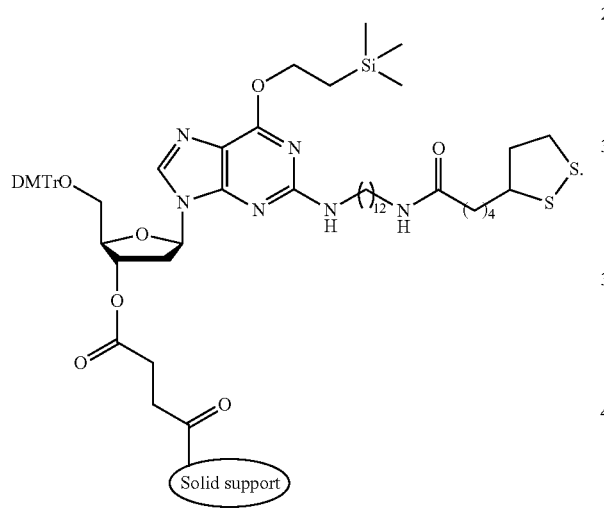

2. A nucleoside, comprising:
a pyrimidine;
a ribose; and
a dithiolane derivative at C5 of the pyrimidine,
wherein the nucleoside is Structure 3 or Structure 4:

Structure 3

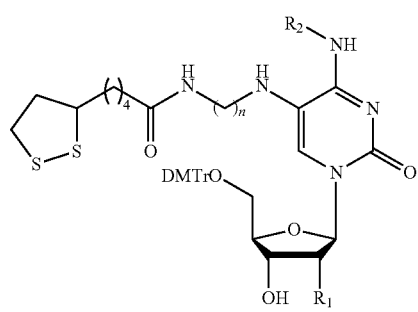

Structure 4

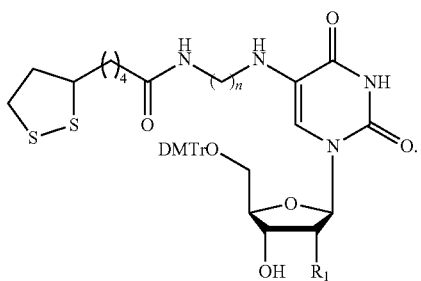

where
$R_1$ is H, OH, F, or O-alkyl,
$R_2$ is Ac, or Bz, and
n is 1-20 carbon atoms.

3. A nucleoside, comprising:
a purine;
a ribose; and
a dithiolane derivative at C8 of the purine,
wherein the nucleoside is Structure 5 or Structure 6:

Structure 5

Structure 6

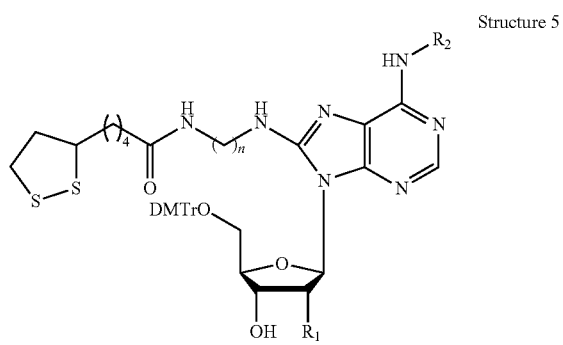

where
$R_1$ is H, OH, F, or O-alkyl,
$R_2$ is Ac, Bz, or DMF,
$R_3$ is cyanoethyl, or ethyltrimethylsily, and
n is 1-20 carbon atoms.

4. A nucleoside, comprising:
a pyrimidine;
a ribose; and
a dithiolane derivative at 2'-O of the ribose,
wherein the nucleoside is Structure 7 or Structure 8:

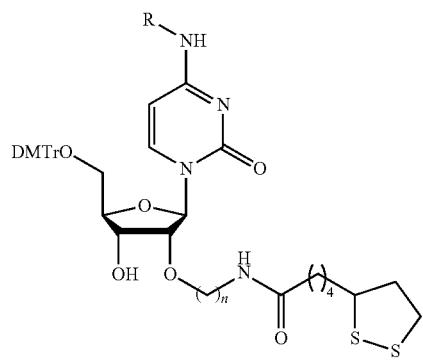

Structure 7

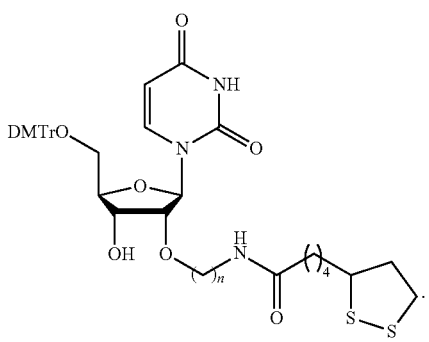

Structure 8 where
R is Ac, Bz, or DMF (dimethyl formamidine), and
n is 1-20 carbon atoms.

5. A nucleoside, comprising:
a purine;
a ribose; and
a dithiolane derivative at 2'O of the ribose,
wherein the nucleoside is Structure 9 or Structure 10:

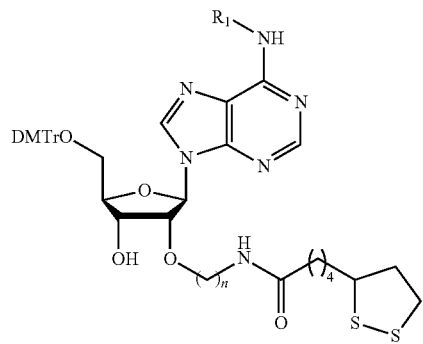

Structure 9

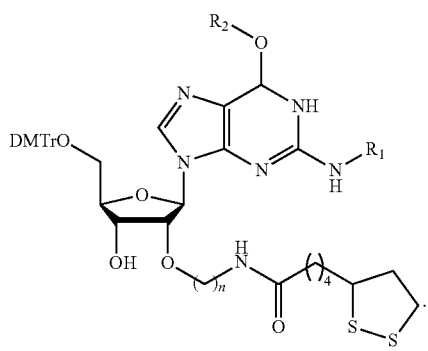

Structure 10 where
$R_1$ is Bz, Ac or DMA,
$R_2$ is ethyltrimethylsilyl, or cyanoethyl, and
n is 1-20 carbon atoms.

6. A nucleoside, comprising:
a pyrimidine;
a ribose;
a dithiolane derivative at C5 of the pyrimidine; and
a phosphoramidite group at 3'-O of the ribose,
wherein the nucleoside is Structure 11 or Structure 12:

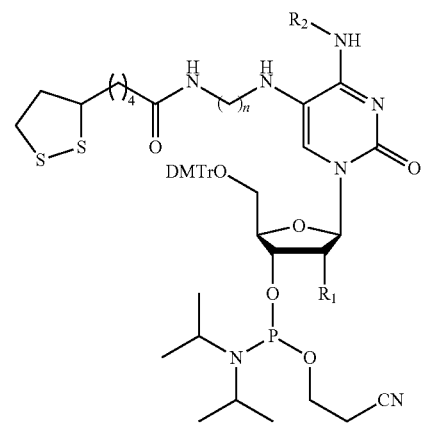

Structure 11

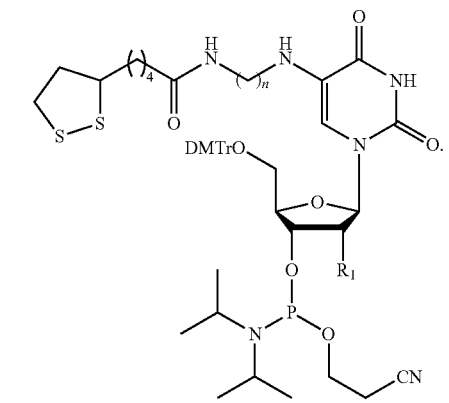

Structure 12 where
$R_1$ is H, OH, F, or O-alkyl,
$R_2$ is Ac, or Bz, and
n is 1-20 carbon atoms.

7. A nucleoside, comprising:
a purine;
a ribose;
a dithiolane derivative at C8 of the purine; and
a phosphoramidite group at 3'-O of the ribose,
wherein the nucleoside is Structure 13 or Structure 14:

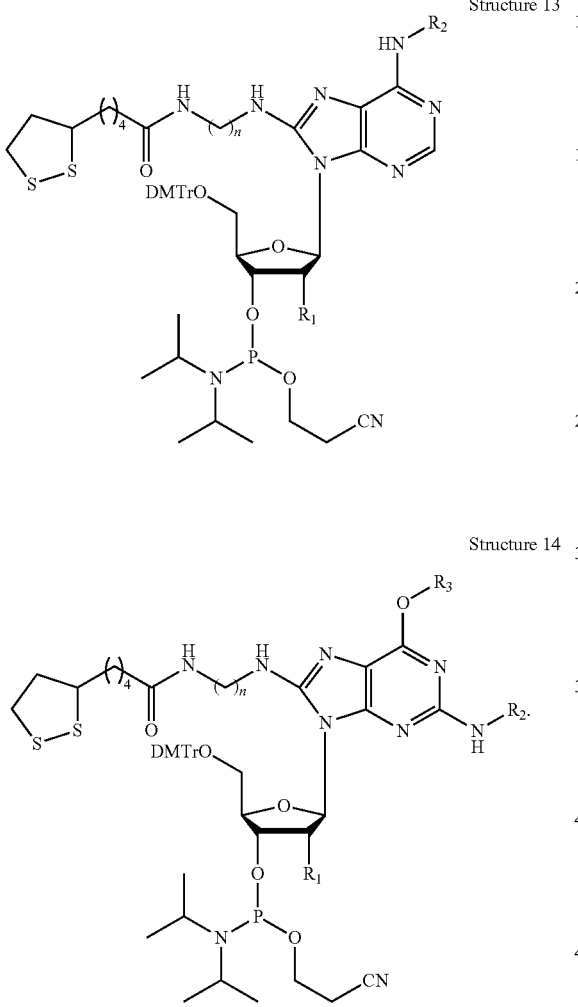

where
$R_1$ is H, OH, F, or O-alkyl,
$R_2$ is Ac, Bz, or DMF,
$R_3$ is cyanoethyl, or ethyltrimethylsilyl, and
n is 1-20 carbon atoms.

8. A nucleoside, comprising:
a pyrimidine;
a ribose;
a dithiolane derivative at 2'-O of the ribose; and
a phosphoramidite group at 3'-O of the ribose,
wherein the nucleoside is Structure 15 or Structure 16:

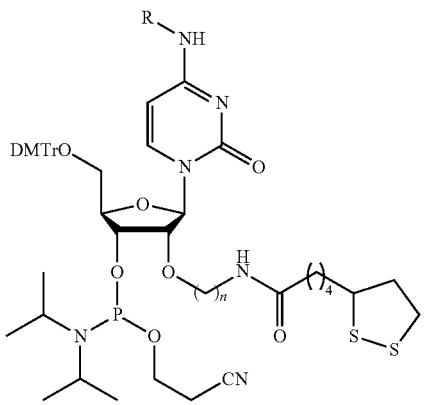

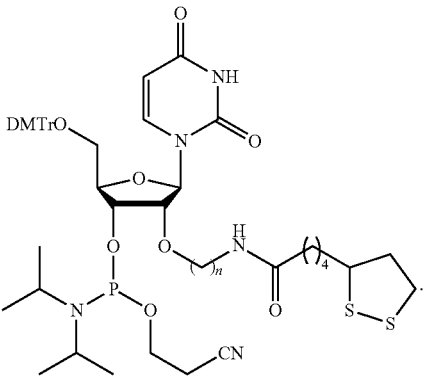

where
R is Ac, Bz, or DMF (dimethyl formamidine), and
n is 1-20 carbon atoms.

9. A nucleoside, comprising:
a purine;
a ribose;
a dithiolane derivative at 2'-O of the ribose; and
a phosphoramidite group at 3'-O of the ribose,
wherein the nucleoside is Structure 17 or Structure 18:

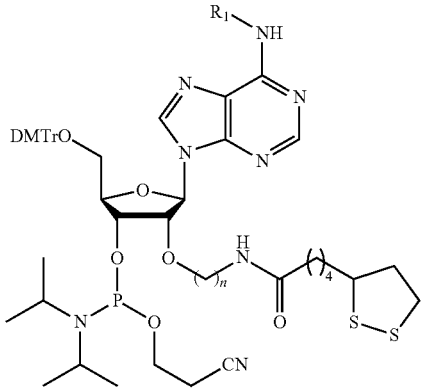

Structure 18

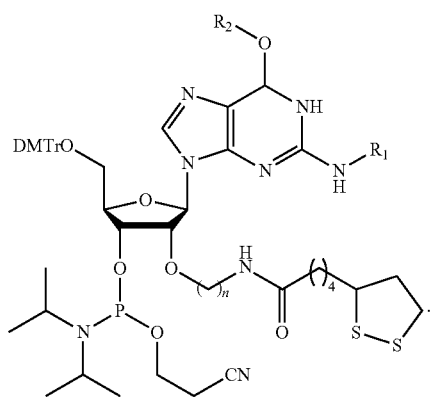

where
R₁ is Bz, Ac, or DMA,
R₂ is ethyltrimethylsilyl, or cyanoethyl, and
n is 1-20 carbon atoms.

10. A nucleoside, comprising:
a ribose;
a succinate group at 3'-O of the ribose; and
a pyrimidine or a purine,
wherein the pyrimidine has a dithiolane derivative at C5 and the pyrimidine is Structure 19 or Structure 20, and
the purine has a dithiolane derive at C8 and is Structure 21 or Structure 22:

Structure 20

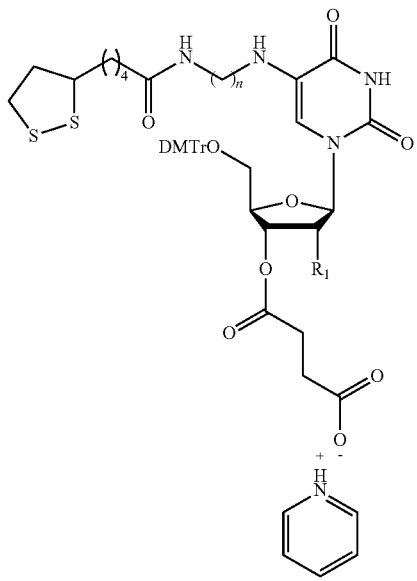

Structure 19

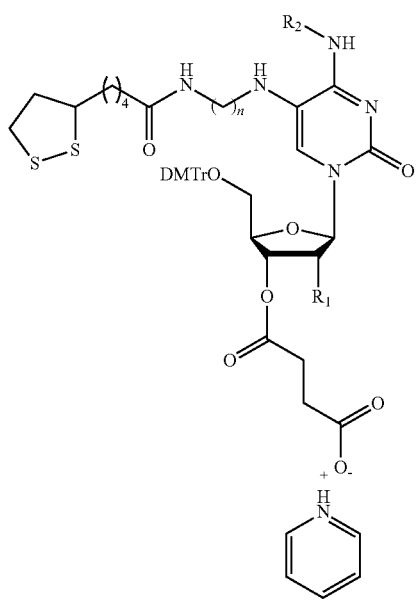

Structure 21

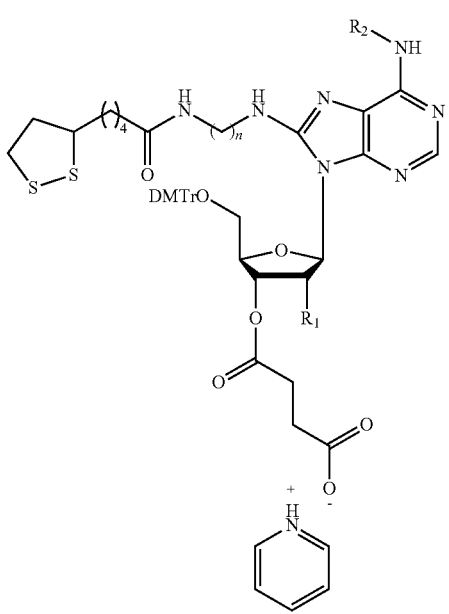

Structure 22

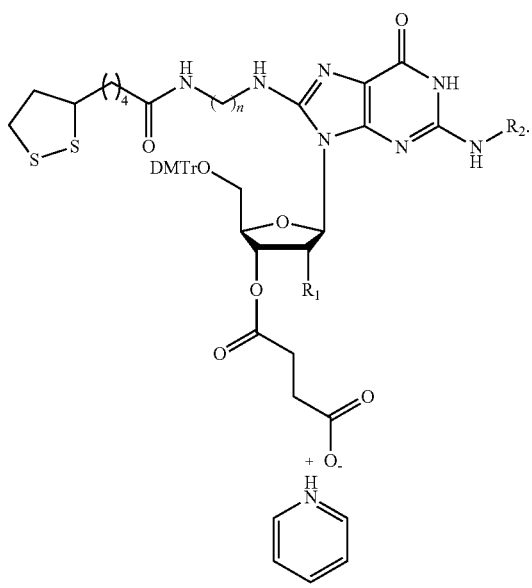

where
R₁ is H, OH, F, or O-alkyl,
R₂ is nucleobase protecting group that is compatible with oligonuleoctide synthesis, and
n is 1-20 carbon atoms 11. A nucleoside, comprising:
a nucleobase;
a ribose;
a dithiolane derivative at 2'-O of the ribose; and
a succinate group at 3'-O of the ribose,
wherein the nucleobase is a pyrimidine or a purine,
wherein the pyrimidine is Structure 23 or Structure 24, and
the purine is Structure 25 or Structure 26:

Structure 23

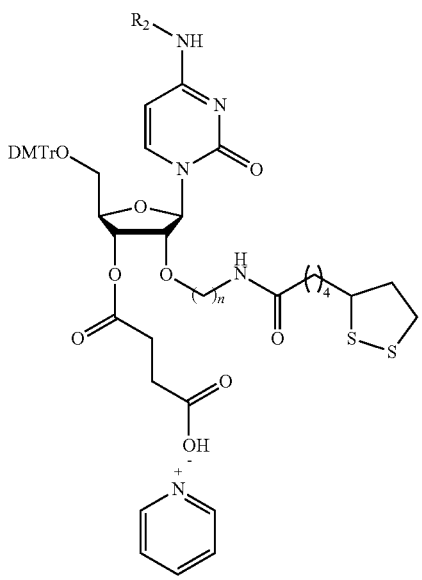

Structure 24

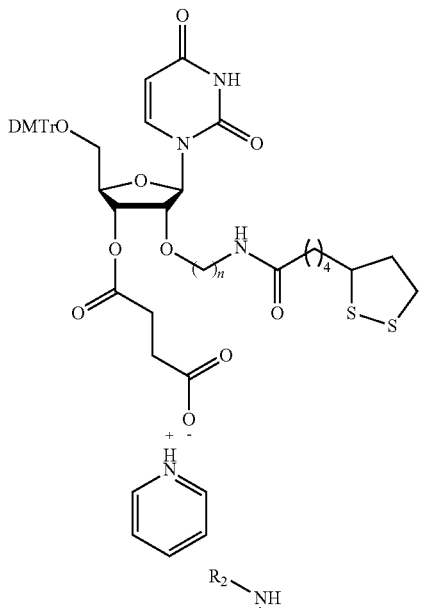

Structure 25

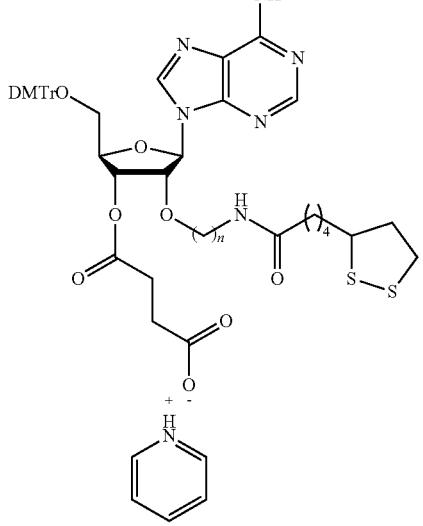

Structure 26

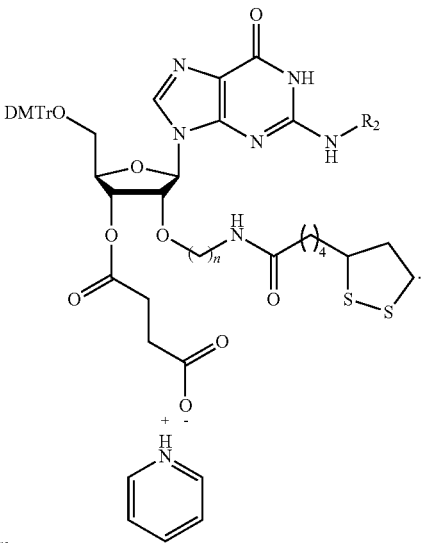

where
R₁ is H, OH, F, or O-alkyl,
R₂ is Bz, Ac, DMF, or DMA, and
n is 1-20 carbon atoms.

12. A nucleoside, comprising:

a nucleobase;

a ribose;

a dithiolane derivative at 2'-O of the ribose; and a solid support at 3'O— of the ribose, wherein the nucleobase is a pyrimidine or a purine, wherein the pyrimidine is Structure 27 or Structure 28, and the purine is Structure 29 or Structure 30:

Structure 27

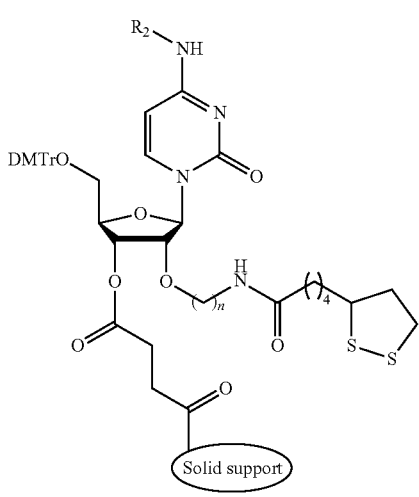

Structure 28

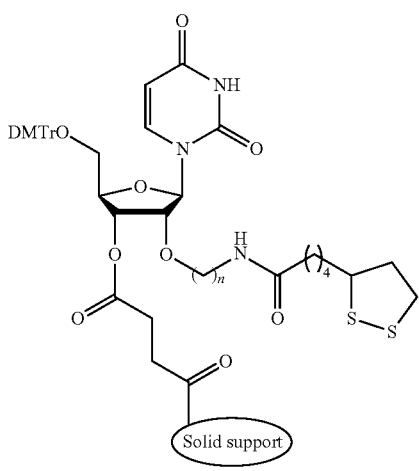

Structure 29

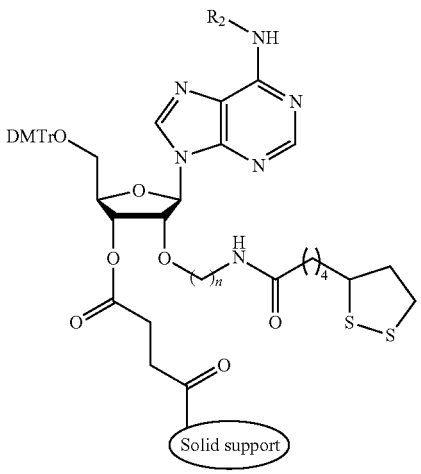

Structure 30

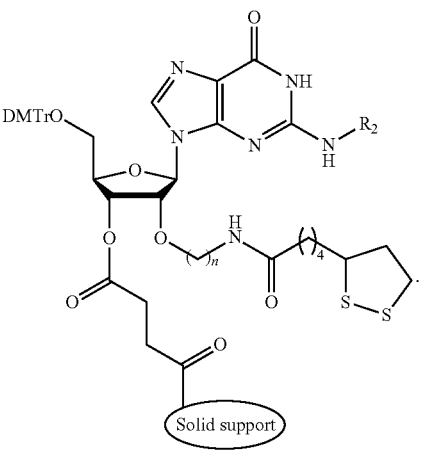

where
$R_1$ is H, OH, F, or O-alkyl,
$R_2$ is Bz, Ac, DMF, or DMA, and
n is 1-20 carbon atoms.

13. A nucleoside, comprising a dithiolane derivative according to any one of claim 1 to claim 12, wherein the nucleoside is one of Structure 1 through Structure 30.

14. A conjugate, comprising:

a plurality of oligonucleotides; and a solid support, wherein each oligonucleotide further comprises the nucleoside of claim 13, and the solid support is gold or quantum dot, and the conjugate is presented in FIG. 14 where each

∿∿∿∿∿∿ is a symbol representing each oligonucleotide.

* * * * *